(12) United States Patent
Goetz et al.

(10) Patent No.: US 7,894,695 B2
(45) Date of Patent: Feb. 22, 2011

(54) TRICYCLIC SPACER SYSTEMS FOR NONLINEAR OPTICAL DEVICES

(76) Inventors: Frederick J. Goetz, 2601 Annand Dr., Suite 16, Wilmington, DE (US) 19808; Frederick J. Goetz, Jr., 2601 Annand Dr., Suite 16, Wilmington, DE (US) 19808

( * ) Notice: Subject to any disclaimer, the term of this patent is extended or adjusted under 35 U.S.C. 154(b) by 540 days.

(21) Appl. No.: 11/666,399

(22) PCT Filed: Oct. 26, 2005

(86) PCT No.: PCT/US2005/039212
§ 371 (c)(1), (2), (4) Date: Apr. 26, 2007

(87) PCT Pub. No.: WO2006/047772
PCT Pub. Date: May 4, 2006

(65) Prior Publication Data
US 2008/0009620 A1 Jan. 10, 2008

Related U.S. Application Data

(60) Provisional application No. 60/622,160, filed on Oct. 26, 2004.

(51) Int. Cl.
C07D 207/40 (2006.01)
C08G 61/02 (2006.01)
G02B 6/00 (2006.01)

(52) U.S. Cl. .......................... 385/122; 528/86; 548/545
(58) Field of Classification Search ................. 385/122; 528/86; 548/545
See application file for complete search history.

(56) References Cited

U.S. PATENT DOCUMENTS 7,621,992 B2 * 11/2009 Ryu et al. ................. 106/31.27
2006/0244801 A1 * 11/2006 Ryu et al. ................... 347/100

FOREIGN PATENT DOCUMENTS

WO   WO-00/09613 A2   2/2000

OTHER PUBLICATIONS

Dimroth, et al., Chemische Berichte, vol. 90, 1957, pp. 1668-1672.*

Cotlet, M. et al., Intramolecular Directional Forster Resonance Energy Transfer at the Single Molecule Level in a Dendritic System., J. Am. Chem. Soc., 2003, vol. 125, pp. 13609-13617.

Mikroyannidis, J.A. et al., "Synthesis by the Gilch Method of Blue-Light-Emitting Poly(p-phenylenevinylene) Derivatives Bearing Highly Phenylate Pendants", Chem. Mater., 2003, vol. 15, pp. 1865-1871.

Mongin, O. et al., "Synthesis and Two-Photon Absorption of Triphenylbenzene-Cored Dendritic Chromophores", Tetrahedron Letters, 2003, vol. 44, pp. 2813-2816.

Spiliopoulos, I. K. et al., "Synthesis of Methacrylic Monomers Bearing Stilbenoid Chromophore and Their Free-Radical Polymerization to Give Luminescent Polymers", Macromolecules, 2002, vol. 35, pp. 7254-7261.

Spiliopoulos, I. K. et al., "Synthesis of Poly(p-phenylene vinylene)- and Poly(phenylene ethynylene)-Based Polymers Containing p-Terphenyl in the Main Chain with Alkoxyphenyl Side Groups", Journal of Polymer Science: Part A: Polymer Chemistry, 2002, vol. 40, pp. 2591-2600.

Maus, M. et al., "Intramolecular Energy Hopping and Energy Trapping in Polyphenylene Dendrimers with Multiple Peryleneimide Donor Chromophores and a Terryleneimide Acceptor Trap Chromophore", J. Am. Chem. Soc., 2001, vol. 123, pp. 7668-7676.

Bonvoisin, J. et al., "Organic Mixed Valence Systems. II. Two-Centers and Three-Centers Compounds with Meta Connections around a Central Phenylene Ring", J. Phys. Chem., 1996, vol. 100, pp. 17079-07082.

* cited by examiner

Primary Examiner—Susannah Chung
(74) Attorney, Agent, or Firm—Connolly Bove Lodge & Hutz LLP

(57) ABSTRACT

A compound for spacing nonlinear optical chromophores of the Formula I

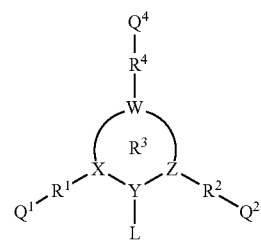

Formula I and the commercially acceptable salts, solvates and hydrates thereof, wherein $R^1$, $R^2$, $R^3$, $R^4$, W, X, Y, Z, $Q^1$, $Q^2$, $Q^4$ and L have the definitions provided herein.

1 Claim, 12 Drawing Sheets

Reactive Alkylating Agent = R-X where R-X is:

--- where -X is:

-Cl,   -Br,   -I,   -OSO$_2$CH$_3$,   -OSO$_2$CF$_3$

,

The ultimate Q-Group introduced is -Q = -OR

Reactive Alkylating Agent = R-X where R-X is:

where -X is:

-Cl,  -Br,  -I,  -OSO$_2$CH$_3$,  -OSO$_2$CF$_3$

The intermediate Q'-Group introduced is -Q' = -OR

| Alkylating Agent | Corresponding Q-Group Produced (Q-RO-) |
|---|---|
|  |  |

Aspect 1 : Q-Groups on Spacer

Aspect 2 : Q-Groups on Chromophore

Aspect 3 : Q-Groups on Spacer and Chromophore

TRICYCLIC SPACER SYSTEMS FOR NONLINEAR OPTICAL DEVICES

RELATED APPLICATIONS

This application is a national stage application (under 35 U.S.C. 371) of PCT/US2005/039212 filed Oct. 26, 2005, which claims benefit of U.S. Provisional application 60/622, 160 filed Oct. 26, 2004.

BACKGROUND OF THE INVENTION

Polymeric electro-optic (EO) materials have demonstrated enormous potential for core application in a broad range of next-generation systems and devices, including phased array radar, satellite and fiber telecommunications, cable television (CATV), optical gyroscopes for application in aerial and missile guidance, electronic counter measure (ECM) systems, backplane interconnects for high-speed computation, ultraquick analog-to-digital conversion, land mine detection, radio frequency photonics, spatial light modulation and all-optical (light-switching-light) signal processing.

Nonlinear optic (NLO) materials are capable of varying their first-, second-, third- and/or higher-order polarizabilities in the presence of an externally applied electric field or incident light (two-photon absorption). In many current telecommunication applications, the second-order polarizability (hyperpolarizability or $\beta$) is of great interest. The hyperpolarizability is related to the change of a NLO material's refractive index in response to application of an electric field. A more complete discussion of nonlinear optical materials may be found in D. S. Chemla and J. Zyss, Nonlinear optical properties of organic molecules and crystals, Academic Press, 1987 and K.-S. Lee, et al. Polymers for Photonics Applications I, Springer (2002)

Many NLO molecules (chromophores) have been synthesized that exhibit extremely high molecular electro-optic properties. The product of the molecular dipole moment ($\mu$) and hyperpolarizability ($\beta$) is often used as a measure of molecular electro-optic performance due to the dipole's involvement in material processing. One chromophore originally evaluated for its extraordinary NLO properties by Bell Labs in the 1960s, Disperse Red (DR), exhibits an electro-optic coefficient $\mu\beta \sim 580 \times 10^{-48}$ esu. Current molecular designs, including FTC, CLD and GLD, exhibit $\mu\beta$ values in excess of $10,000 \times 10^{-48}$ esu. See Dalton et al., "New Class of High Hyperpolarizability Organic Chromophores and Process for Synthesizing the Same", WO 00/09613.

Nevertheless extreme difficulties have been encountered translating microscopic molecular hyperpolarizabilities ($\beta$) into macroscopic material hyperpolarizabilities ($\chi^{(2)}$). Molecular subcomponents (chromophores) must be integrated into NLO materials that exhibit (i) a high degree of macroscopic nonlinearity and (ii) sufficient temporal, thermal, chemical and photochemical stability. Simultaneous solution of these dual issues is regarded as the final impediment in the broad commercialization of EO polymers in numerous government and commercial devices and systems.

The production of high material hyperpolarizabilities ($\chi^{(2)}$) is limited by the poor social character of NLO chromophores. Commercially viable materials must incorporate chromophores at large molecular densities with the requisite molecular moment statistically oriented along a single material axis. In order achieve such an organization, the charge transfer (dipole) character of NLO chromophores is commonly exploited through the application of an external electric field during material processing that creates a localized lower-energy condition favoring noncentrosymmetric order. Unfortunately, at even moderate chromophore densities, molecules form multi-molecular dipolarly-bound (centrosymmetric) aggregates that cannot be dismantled via realistic field energies. To overcome this difficulty, integration of anti-social dipolar chromophores into a cooperative material architecture is commonly achieved through the construction of physical barriers that limit proximal intermolecular relations. This has been successfully accomplished through (i) surrounding individual molecules with sterically hindering constituents or (ii) covalently binding molecules to secondary organizing superstructures such as on polymeric backbones or within dendrimeric formations. Other methods, such as self-assembling superlattices, have been proposed by Tobin Marks and others but are unlikely to produce near-term macroscopically-useful results. See K.-S. Lee, et al. (2002); Keinan S. et al., Chem. Mater., 16, 1848-1854 (2004); Koeckelberghs, G. et al., Marcromolecules, 36, 9736-9741 (2003); Robinson, B. H. et al. J. Phys. Chem. A, 104, 4785-4795 (2000); L. Dalton et al., "The Role of London Forces in Defining Noncentrosymmetric Order of High Dipole Moment-High Hyperpolarizability Chromophores in Electrically Poled Polymeric Films", Proceedings of the National Academy of Sciences USA, Vol. 94, pp. 4842-4847 (1997).

Nevertheless, the most daunting problem in the production of commercially successful NLO polymers is the issue of resultant long-term material stability. Although molecular organization techniques have produced extremely high-performance materials (exhibiting sub-1-volt drive voltages and switching frequencies in excess of 100 Gb/s), the manufacture of a commercial quality high-stability polymer-based devices operating at even 10 Gb/s is only now on the verge of reality. See, L. Dalton et al., "Synthesis and Processing of Improved Organic Second-Order Nonlinear Optical Materials for Applications in Photonics", Chemistry of Materials, Vol. 7, No. 6, pp. 1060-1081 (1995); and Shi Y. et al., Science, 288, 119-121. This failing is primarily due to the reinstitution of centrosymmetry as a result of molecular mobility over time. Three solutions have been envisioned to resolve this issue: (i) incorporation of chromophores in high glass transition (Tg) host polymers; (ii) backbone and dendrimeric single-point polymer integration; and (iii) multi-point crosslinked integration. The use of high $T_g$ polymers has yet to show satisfactory results due to thermal-induced nucleophilic degradation of NLO chromophores. Single-point integration techniques wherein the chromophore is attached to a polymeric superstructure via one point on the chromophore (usually on the electron donating amine) have similarly demonstrated insufficient thermal character presumably due to the residual latitude of molecular mobility; in addition to thermal randomization, mobility is partially induced over operation lifetime by motion as a result of photo-stimulated cis-trans isomerization. Multi-point and double-ended crosslinked (DEC) integration strategies are the only techniques that have demonstrated the ability to meet thermal requirements. See Kajzar, F. et al. Organic Thin Films for Waveguding Nonlinear Optics, Gordon (1996).

Thus, the effectiveness of organic NLO materials having high hyperpolarizabilities is limited by the tendency of these materials to aggregate when processed as well as the thermal stability of those resultant materials. Accordingly, there exists a need for improved nonlinear optically active materials having large hyperpolarizabilities and that when employed in electro-optic devices, exhibit large electro-optic coefficients and high thermal stability. The present invention seeks to fulfill these needs and provides further related advantages by introducing spacer systems that separate individual chromophores thereby preventing aggregation and providing for multi-point material integration for long-term thermal stability.

SUMMARY OF THE INVENTION

The present invention relates to compounds for spacing nonlinear optical chromophores of the Formula I

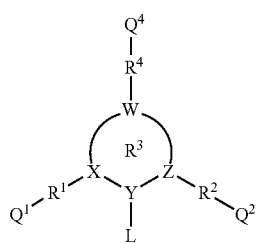

Formula I or a commercially acceptable salt thereof; wherein $R_3$ is a $C_6$-$C_{10}$ aryl, $C_6$-$C_{10}$ heteroaryl, 4-10 membered heterocyclic or a $C_6$-$C_{10}$ saturated cyclic group; 1 or 2 carbon atoms in the foregoing cyclic moieties are optionally substituted by an oxo (=O) moiety; and the foregoing $R^3$ groups are optionally substituted by 1 to 3 $R^5$ groups;

$R_1$ and $R_2$ are independently selected from the list of substituents provided in the definition of $R_3$, $(CH_2)_t(C_6$-$C_{10}$ aryl) or $(CH_2)_t$(4-10 membered heterocyclic), t is an integer ranging from 0 to 5, and the foregoing $R_1$ and $R_2$ groups are optionally substituted by 1 to 3 $R^5$ groups;

$R_4$ is independently selected from the list of substituents provided in the definition of $R_3$, a chemical bond (—), or hydrogen;

each $Q^1$, $Q^2$, and $Q^4$ is independently selected from hydrogen, halo, $C_1$-$C_{10}$ alkyl, $C_2$-$C_{10}$ alkenyl, $C_2$-$C_{10}$ alkynyl, nitro, trifluoromethyl, trifluoromethoxy, azido, —$OR^5$, —$NR^6C(O)OR^5$, —$NR^6SO_2R^5$, —$SO_2NR^5R^6$, —$NR^6C(O)R^5$, —$C(O)NR^5R^6$, —$NR^5R^6$, —$S(O)_jR^7$ wherein j is an integer ranging from 0 to 2, —$NR^5(CR^6R^7)_tOR^6$, —$(CH_2)_t(C_6$-$C_{10}$ aryl), —$SO_2(CH_2)_t(C_6$-$C_{10}$ aryl), —$S(CH_2)_t(C_6$-$C_{10}$ aryl), —$O(CH_2)_t(C_6$-$C_{10}$ aryl), —$(CH_2)_t$(4-10 membered heterocyclic), and —$(CR^6R^7)_mOR^6$, wherein m is an integer from 1 to 5 and t is an integer from 0 to 5; with the proviso that when $R^4$ is hydrogen $Q^4$ is not available; said alkyl group optionally contains 1 or 2 hetero moieties selected from O, S and —N($R^6$)— said aryl and heterocyclic Q groups are optionally fused to a $C_6$-$C_{10}$ aryl group, a $C_5$-$C_8$ saturated cyclic group, or a 4-10 membered heterocyclic group; 1 or 2 carbon atoms in the foregoing heterocyclic moieties are optionally substituted by an oxo (=O) moiety; and the alkyl, aryl and heterocyclic moieties of the foregoing Q groups are optionally substituted by 1 to 3 substituents independently selected from nitro, trifluoromethyl, trifluoromethoxy, azido, —$NR^6SO_2R^5$, —$SO_2NR^5R^6$, —$NR^6C(O)R^5$, —$C(O)NR^5R^6$, —$NR^5R^6$, —$(CR^6R^7)_mOR^6$ wherein m is an integer from 1 to 5, —$OR^5$ and the substituents listed in the definition of $R^5$;

each $R^5$ is independently selected from H, $C_1$-$C_{10}$ alkyl, —$(CH_2)_t(C_6$-$C_{10}$ aryl), and —$(CH_2)_t$(4-10 membered heterocyclic), wherein t is an integer from 0 to 5; said alkyl group optionally includes 1 or 2 hetero moieties selected from O, S and —N($R^6$)— said aryl and heterocyclic $R^5$ groups are optionally fused to a $C_6$-$C_{10}$ aryl group, a $C_5$-$C_8$ saturated cyclic group, or a 4-10 membered heterocyclic group; and the foregoing $R^5$ substituents, except H, are optionally substituted by 1 to 3 substituents independently selected from nitro, trifluoromethyl, trifluoromethoxy, azido, —$NR^6C(O)R^7$, —$C(O)NR^6R^7$, —$NR^6R^7$, hydroxy, $C_1$-$C_6$ alkyl, and $C_1$-$C_6$ alkoxy;

each $R^6$ and $R^7$ is independently H or $C_1$-$C_6$ alkyl;

X, Y and Z are each independently selected from C (carbon), O (oxygen), N (nitrogen), and S (sulfur), and are included within $R^3$;

X, Y, and Z are immediately adjacent to one another;

W is any non-hydrogen atom in $R^3$ that is not X, Y, or Z; and

L is a labile group or a nonlinear optical chromophore.

An embodiment of the present invention refers to the following compounds:

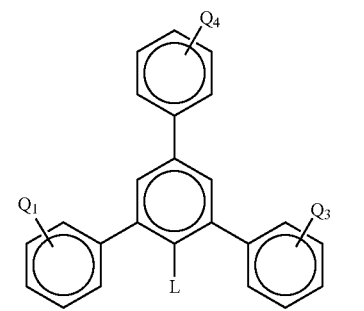

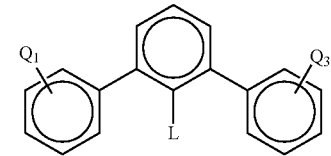

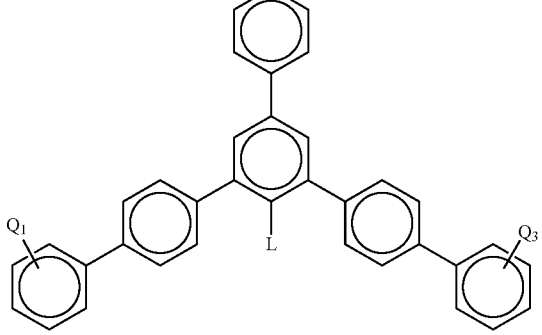

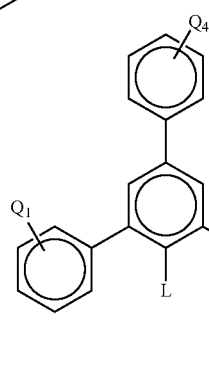

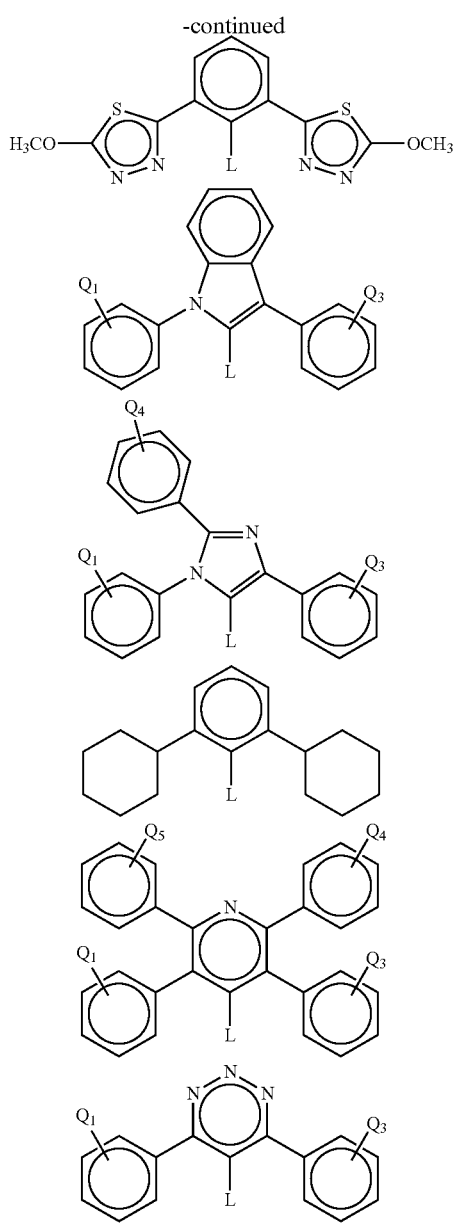

In this invention the term "nonlinear optic chromophore" (NLOC) is defined as molecules or portions of a molecule that create a nonlinear optic effect when irradiated with light. The chromophores are any molecular unit whose interaction with light gives rise to the nonlinear optical effect. The desired effect may occur at resonant or nonresonant wavelengths. The activity of a specific chromophore in a nonlinear optic material is stated as their hyper-polarizability, which is directly related to the molecular dipole moment of the chromophore.

In this invention, the term "labile groups," unless otherwise indicated, is defined as transitory molecular entities, or groups, which can be replaced with other molecular entities under specified conditions to yield a different functionality.

Examples of specific labile groups include, but are not limited to protons (—H), hydroxyl groups (—OH), alkoxy groups (—OR), nitro groups (—NO$_2$), amine (—NHO) and halogens. Labile groups may be attached to other molecular entities, including, but not limited to, aromatic and substituted aromatic cyclic structures, oxygen containing moieties, carbonyl containing moieties, and thiophene containing moieties, or mixtures thereof.

In this invention, the term "halo," unless otherwise indicated, includes fluoro, chloro, bromo or iodo. Preferred halo groups are fluoro, chloro and bromo.

The term "alkyl," as used herein, unless otherwise indicated, includes saturated monovalent hydrocarbon radicals having straight, cyclic or branched moieties. It is understood that for cyclic moieties at least three carbon atoms are required in said alkyl group.

The term "alkenyl," as used herein, unless otherwise indicated, includes monovalent hydrocarbon radicals having at least one carbon-carbon double bond and also having straight, cyclic or branched moieties as provided above in the definition of "alkyl."

The term "alkynyl," as used herein, unless otherwise indicated, includes monovalent hydrocarbon radicals having at least one carbon-carbon triple bond and also having straight, cyclic or branched moieties as provided above in the definition of "alkyl."

The term "alkoxy," as used herein, unless otherwise indicated, includes O-alkyl groups wherein "alkyl" is as defined above.

The term "aryl," as used herein, unless otherwise indicated, includes an organic radical derived from an aromatic hydrocarbon by removal of one hydrogen, such as phenyl or naphthyl.

The term "heteroaryl," as used herein, unless otherwise indicated, includes an organic radical derived by removal of one hydrogen atom from a carbon atom in the ring of a heteroaromatic hydrocarbon, containing one or more heteroatoms independently selected from O, S, and N. Heteroaryl groups must have at least 5 atoms in their ring system and are optionally substituted independently with 0-2 halogen, trifluoromethyl, $C_1$-$C_6$ alkoxy, $C_1$-$C_6$ alkyl, or nitro groups.

The term "4-10 membered heterocyclic," as used herein, unless otherwise indicated, includes aromatic and non-aromatic heterocyclic groups containing one or more heteroatoms each selected from O, S and N, wherein each heterocyclic group has from 4-10 atoms in its ring system. Non-aromatic heterocyclic groups include groups having only 4 atoms in their ring system, but aromatic heterocyclic groups must have at least 5 atoms in their ring system. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The term "saturated cyclic group" as used herein, unless otherwise indicated, includes non-aromatic, fully saturated cyclic moieties wherein alkyl is as defined above.

The phrase "commercially acceptable salt(s)", as used herein, unless otherwise indicated, includes salts of acidic or basic groups which may be present in the compounds of the invention. The compounds of the invention that are basic in nature are capable of forming a wide variety of salts with various inorganic and organic acids. The acids that may be used to prepare pharmaceutically acceptable acid addition salts of such basic compounds of the invention are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the invention that are acidic in nature are capable of forming base salts with various pharmacologically acceptable cations. Examples of such salts include the alkali metal or alkaline earth metal salts and particularly the sodium and potassium salts.

The term "solvate," as used herein includes a compound of the invention or a salt thereof, that further includes a stoichiometric or non-stoichiometric amount of a solvent bound by non-covalent intermolecular forces.

The term "hydrate," as used herein refers to a compound of the invention or a salt thereof, that further includes a stoichiometric or non-stoichiometric amount of water bound by non-covalent intermolecular forces.

Certain compounds of the present invention may have asymmetric centers and therefore appear in different enantiomeric forms. This invention relates to the use of all optical isomers and stereoisomers of the compounds of the invention and mixtures thereof. The compounds of the invention may also appear as tautomers. This invention relates to the use of all such tautomers and mixtures thereof.

The subject invention also includes isotopically-labelled compounds, and the commercially acceptable salts thereof, which are identical to those recited in Formulas I and II but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds of the present invention and commercially acceptable salts of said compounds which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain advantages resulting from greater stability. Isotopically labelled compounds of Formula I of this invention can generally be prepared by carrying out the procedures disclosed in the Schemes and/or in the Examples and Preparations below, by substituting a readily available isotopically labelled reagent for a non-isotopically labelled reagent Each of the patents, patent applications, published International applications, and scientific publications referred to in this patent application is incorporated herein by reference in its entirety.

DETAILED DESCRIPTION OF THE INVENTION

The compounds of Formula I are useful as agents, for spacing nonlinear optical chromophores to prevent the chromophores from aggregating. Many useful NLO chromophores are known to those of ordinary skill in the art. While any NLO chromophore that provides the desired NLO effect and is compatible with the synthetic methods used to form the NLO spacer/chromophore may be used in the present invention, preferred NLO chromophores include an electron donating group and an electron withdrawing group.

Figure 1:
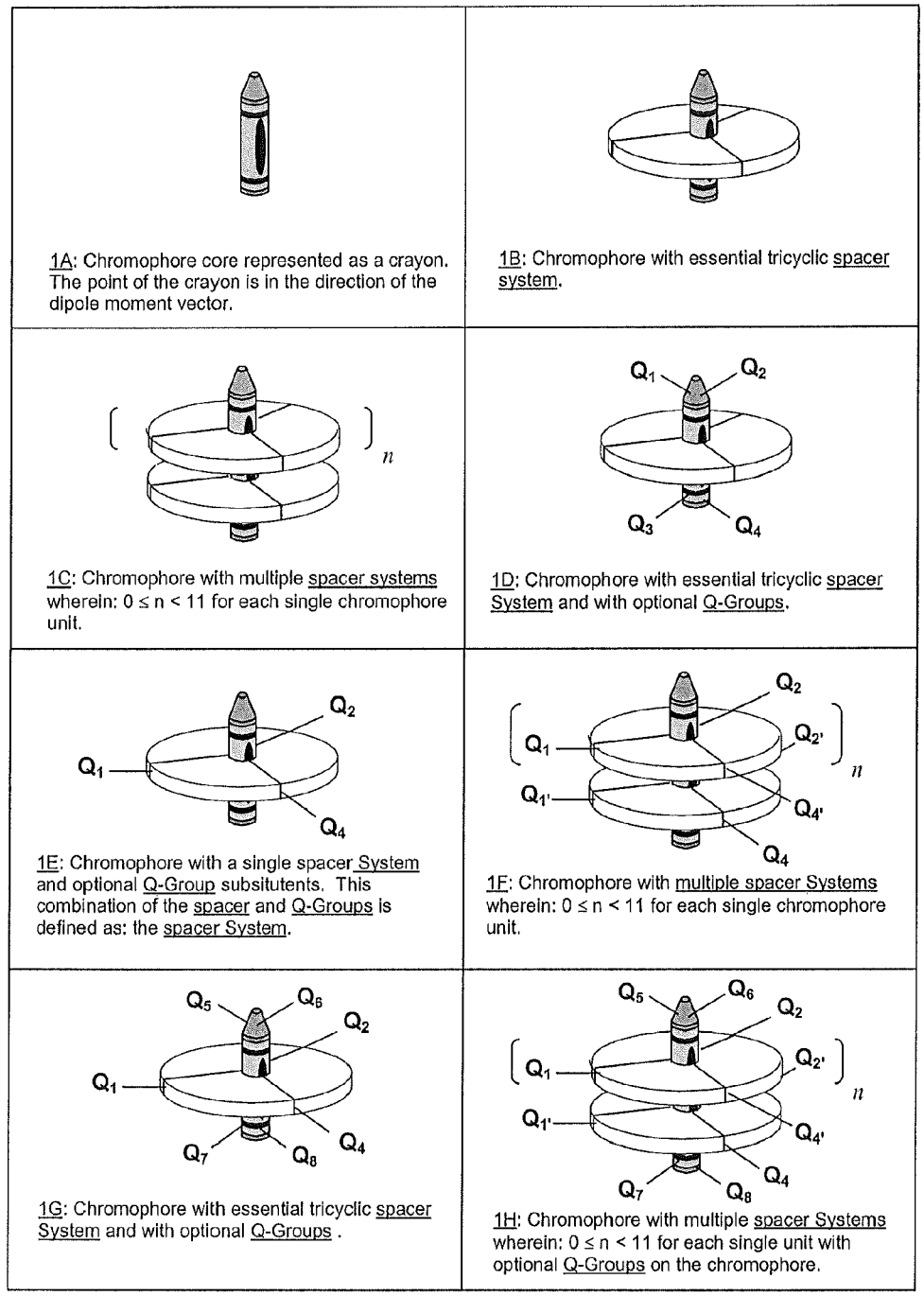
FIG. 1 A general representation of the spacer systems of the present invention wherein the chromophore is represented as a crayon in 1A.
Figure 2:
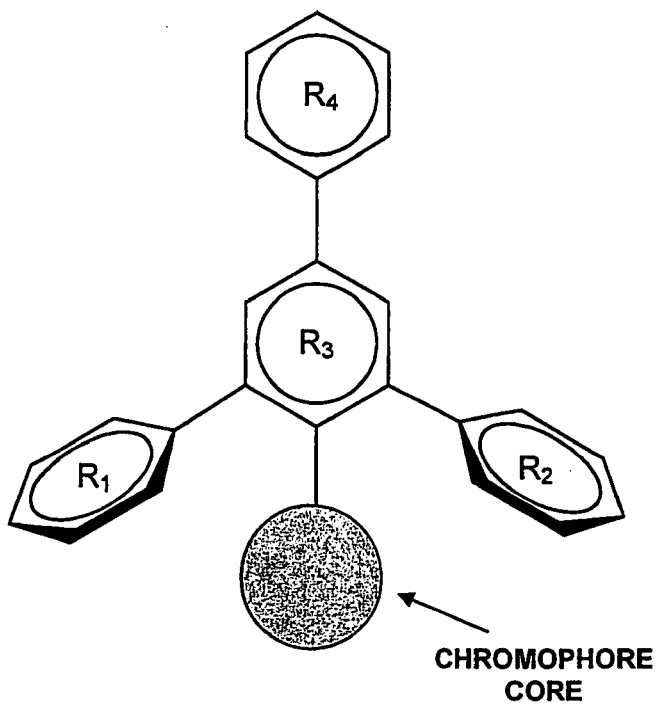
FIG. 2 Schematic representation of spacer system with attached chromophore core.

FIG. 1 presents in a general fashion the tricyclic structure of the chromophore spacer system of the present invention. Typically, the spacer, which consists of $R^1$, $R^2$ and $R^3$, is attached to a non-linear optical chromophore, L in FIG. 1, near the center of the chromophore rather than the end of the chromophore. The spacer effectively wraps around the chromophore L to create a small void space V that prevents other molecular species, including solvents, from interacting with the chromophore. Consequently, the spacer $R^1$, $R^2$ and $R^3$, protects the chromophore L from physical contact and chemical attack by molecular species which may interfere with the electronic properties of the chromophore. In addition, the spacers effectively prevent the active chromophores from aggregating in the common head-to-tail pattern during processing. In certain embodiments of the present invention a fourth ring system $R^4$ may be added to the spacer $R^1$, $R^2$ and $R^3$, at the $R^3$ position to provide additional separation between the individual chromophores. FIG. 2 illustrates a spacer system incorporating all four ring moieties $R^1$, $R^2$, $R^3$, and $R^4$.

Essential to all subject systems of this Invention is the spacer system shown in 1B individually and multiply in 1C. Shown in 1D is the essential component on a chromophore substituted with optional Q-Groups. Shown in 1E, 1F, 1G and 1H are Q-Groups that are substituted. All systems illustrated as 1B, 1C, 1D, 1E, 1F, 1G and 1H lie within the scope of this Invention for Level 1 applications.

Figure 3:
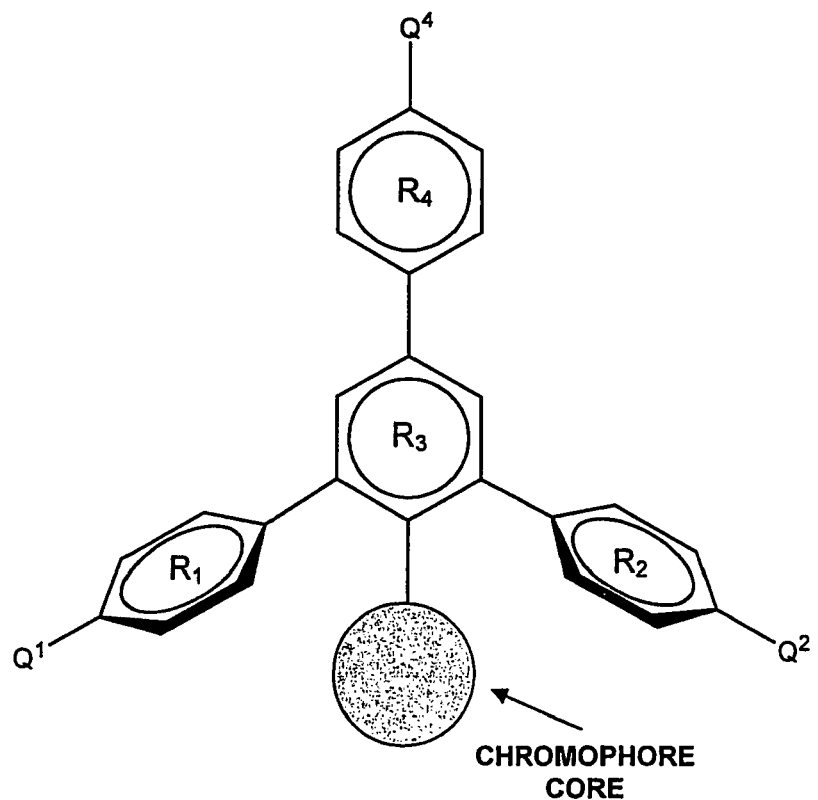
FIG. 3 Schematic representation of spacer system having attached Q group functionality and attached chromophore.

The various cyclic moieties of the spacer $R^1$, $R^2$, $R^3$, and $R^4$ may incorporate additional functional groups Q that add thermal stability to the spacer/chromophore system and also allow the spacer to serve as a polymeric monomer capable of being inserted into any of a number of polymer systems including polyamides, polyimides, polyesters, etc. FIG. 3 shows a terphenyl spacer with functional groups Q1, Q2 and Q4 attached to the peripheral cyclic moieties R1, R2 and R4 respectively. In one embodiment the individual Q groups may be selected from substituents that become chemically reactive during poling processes that align the chromophores, such that the individual Q groups polymerize with one another creating a nonlinear optical polymer with engineered spacing between the chromophores.

Figure 4:
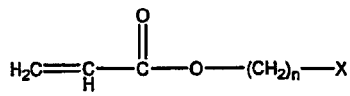
FIG. 4 Nonlimiting Examples of Specific Polymerizable Functionality Introduced with Reactive Alkylating Agents.
Figure 4:
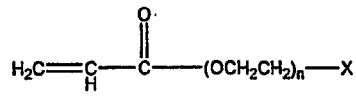
Figure 4:
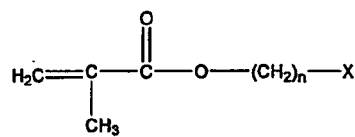
Figure 4:
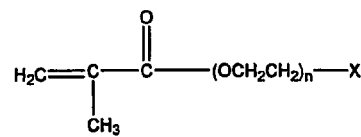
Figure 4:
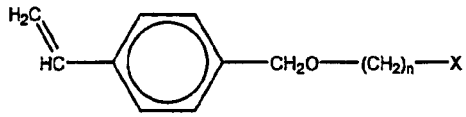
Figure 4:
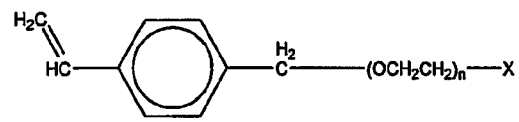
Figure 4:
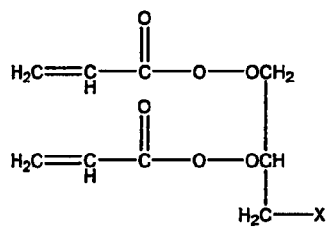
Figure 4:
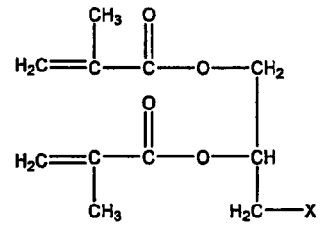
Figure 4:
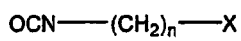
Figure 4:
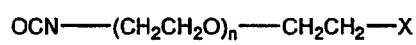
Figure 4:
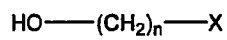
Figure 4:
Figure 4:
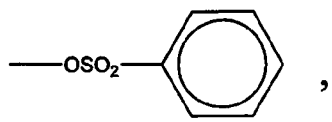
Figure 4:
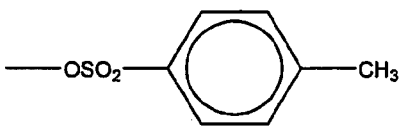
Figure 5:
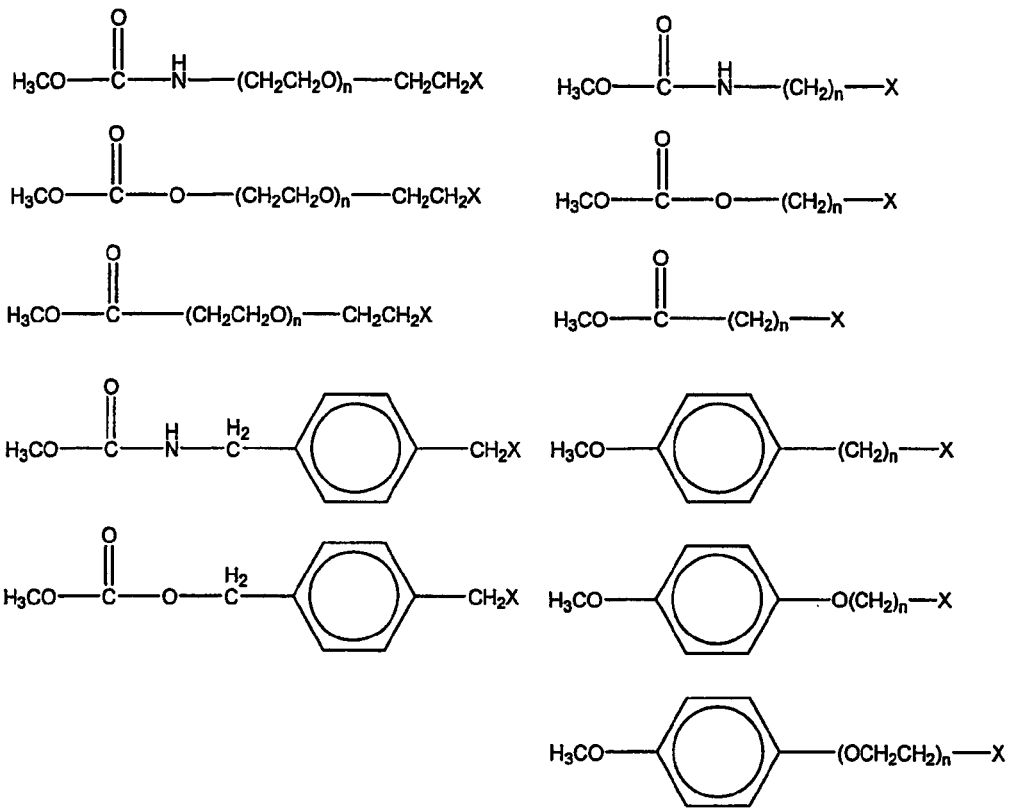
FIG. 5 Nonlimiting Examples of Specific Functionality Capable of Secondary Bonding for Applications Introduced with Reactive Alkylating Agents.
Figure 5:
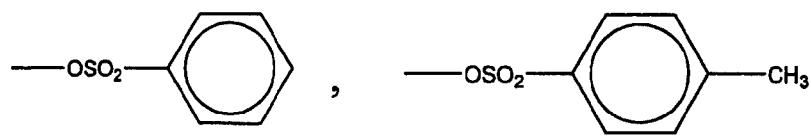
Figure 6:
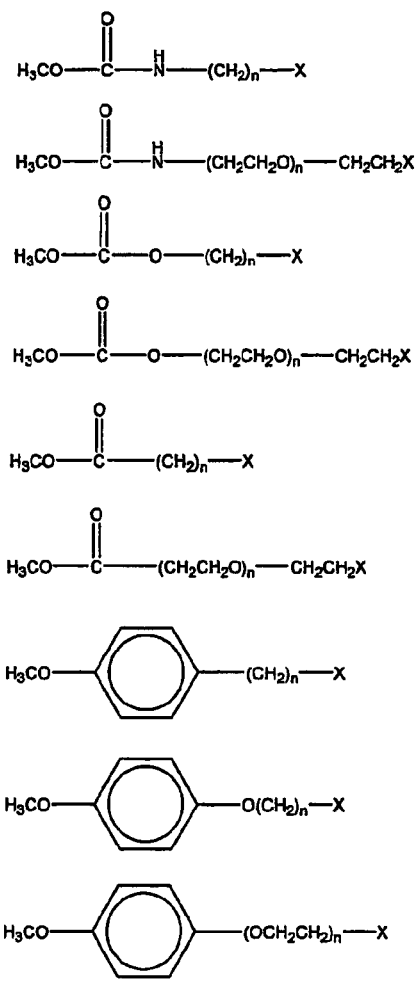
FIG. 6 Nonlimiting Examples of Specific Functionality Capable of Secondary Bonding by Condensation Polymerization Crosslinking Approaches through Block/Deblock Technology Employing the Reactive Alkylating Agents as Key Intermediates.
Figure 6:
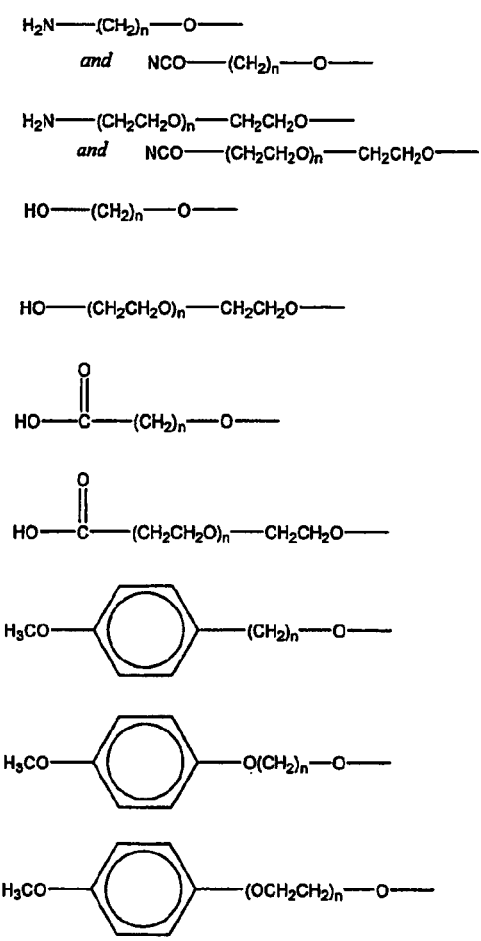
Figure 7:
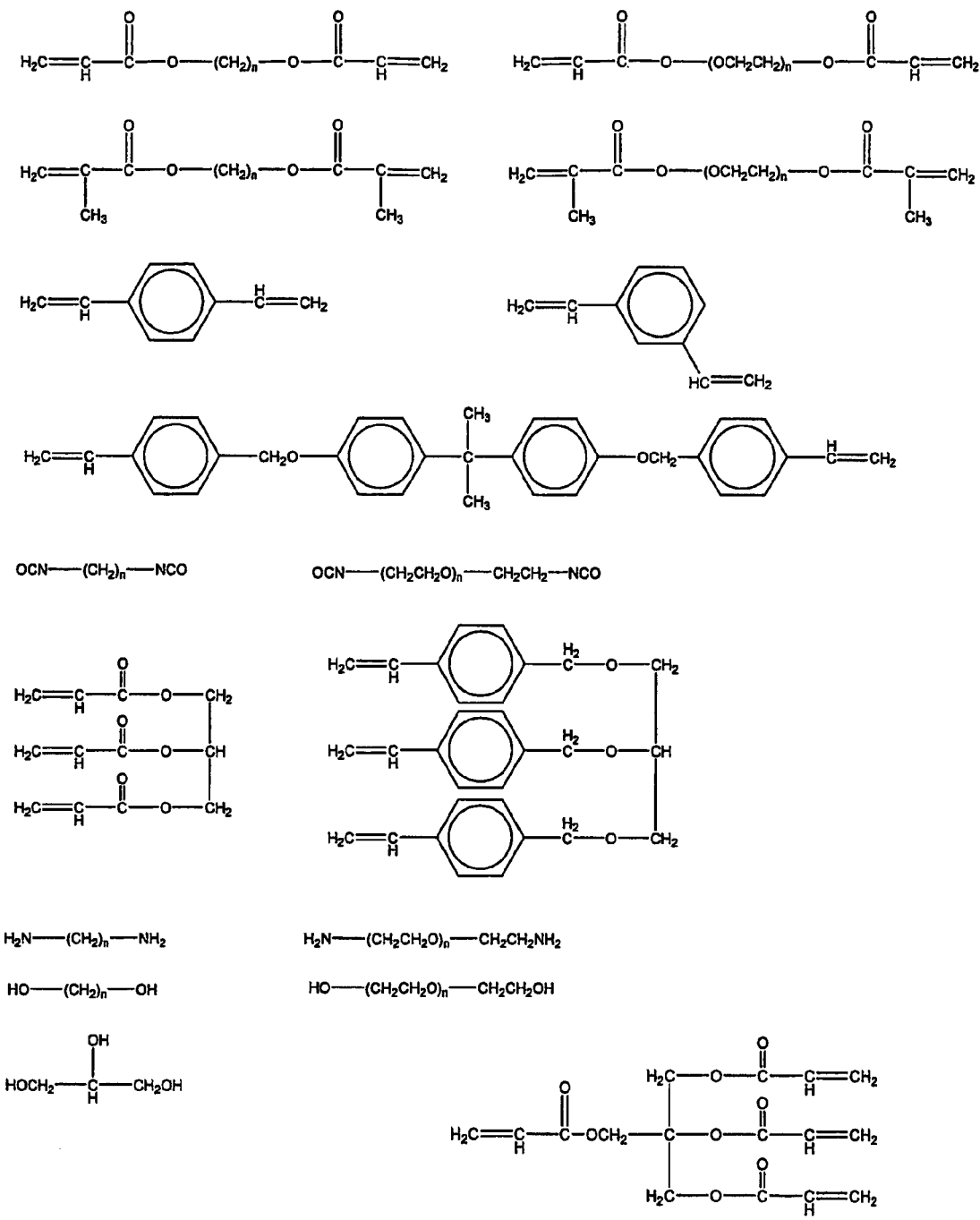
FIG. 7 Nonlimiting Conventional Crosslinking Agents Applicable to the Production of Crosslinked Materials.
Figure 14:
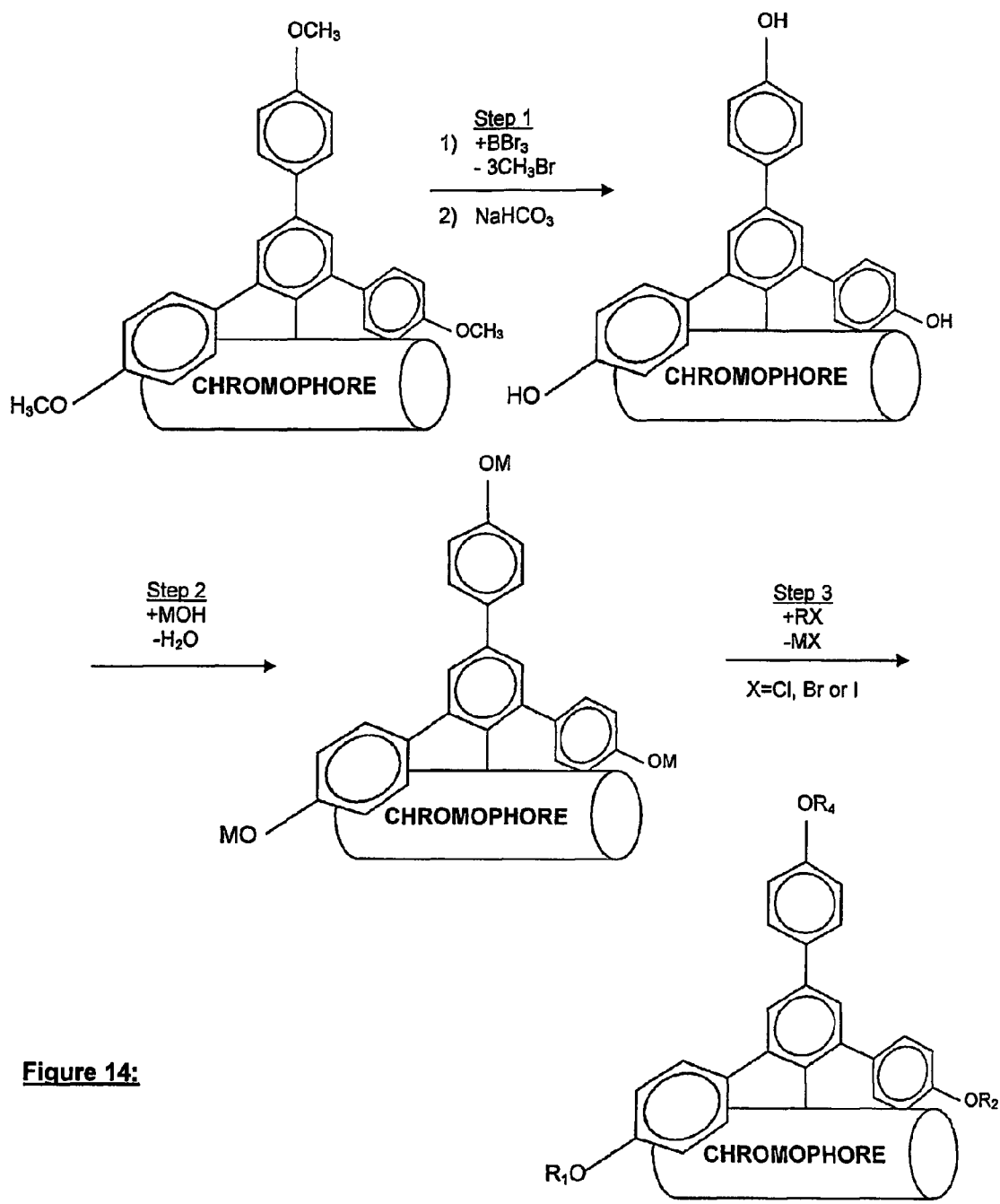
FIG. 14 Specific Nonlimiting Examples of Application of Conventional Block-Deblock Techniques for Q-Functionalization of methoxylated spacer 4'-Phenyl-m-Terphenyl Systems.

Nonlimiting examples of Q groups capable of providing polymerizable functionality to the spacer are provided in FIG. 4. The functional groups listed in FIG. 4 may be introduced to the spacer as reactive alkylating agents. Additional functional groups that serve as potential Q groups are listed in FIG. 5. The functional groups of FIG. 5 may also be introduced to the spacer as reactive alkylating agents in a block/deblock process as shown in FIG. 14. High stability methoxy blocking groups may be terminally located at various points of the spacer systems. Chemical methods well-known to those skilled in the art may be used to replace or "deblock" these groups with more reactive hydroxy constituents which may in turn be easily replaced with a broad variety of R-groups. Additional functionality that may serve as Q groups include the various monomers from polymer condensation reactions. FIGS. 5, 6 and 7 include nonlimiting examples of various functional groups that are known monomers that may be used as Q groups to link spacers with attached chromophores.

A nonlimiting list of potential Q groups are provide in FIGS. 4-8. The salt is reacted with an appropriate alkylating agent, RX, to introduce the desired Q-Group functionality wherein $Q=^-OR$. Such processes are well known to those skilled-in-the-art.

Figure 8:
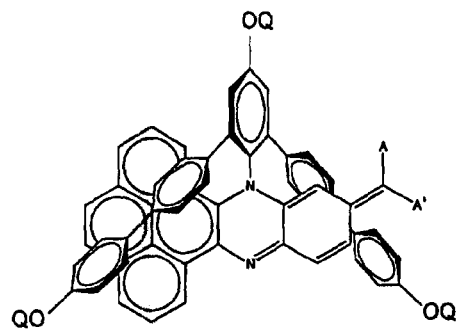
FIG. 8 Structural illustration depicting Q group attachment on the spacer, the chromophore or a combination thereof.
Figure 8:
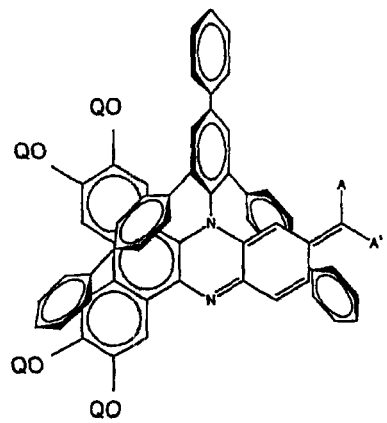
Figure 8:
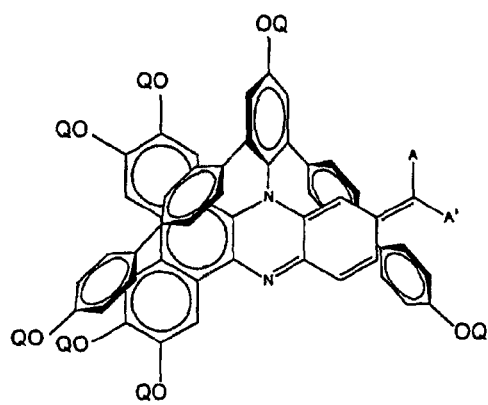

FIG. 8 illustrates that the Q groups can be attached to any portion of the spacer/chromophore system including R1, R2, R3, R4 and the chromophore. If reactive functional groups are placed on the R1 and R2 rings then a string of spacer/chromophore monomers can be attached in a polymeric fashion. If reactive functional groups are also attached to the R4 group crosslinking is encouraged and may be managed to some extent in the poling process. Crosslinking produces thermally stable organic optical materials. An increase in nonlinear optical properties can also be expected due to the manufacture of aligned chromophores in the poling process. The chromophores are aligned in the optimal orientation for optical activity and locked into place during the crosslinking process.

The compounds of Formula I may be prepared according to the following reaction schemes and discussions. The reaction schemes provide specific non-limiting examples of the manufacture of tricyclic spacer systems of the present invention. Each scheme demonstrates the structure common to all spacer systems of the present invention which is a central or primary cyclic structure, $R^3$, having three atoms X, Y, and Z that are directly bonded to one another and where secondary cyclic moieties $R^1$ and $R^2$ are bound to atoms X and Z respectively. FIGS. 2 and 3 illustrate generically the relationship between the X, Y and Z atoms of $R^3$ and the cyclic moieties of $R^1$ and $R^2$. Specific examples of the spatial relationship between $R^1$, $R^2$ and $R^3$ are illustrated in schemes 1 and 2. Unless otherwise indicated, $R^1$, $R^2$, $R^3$, $R^4$, $R^5$, $R^6$, W, X, Y, Z, $Q^1$, $Q^2$, $Q^4$, and L in the reaction scheme and discussion that follow are as defined above.

Scheme 1: Conventional Process for the Production of a Key Intermediate for the Introduction of the 4'-Phenyl-m-Terphenyl Functionality: A Substituted 4'-Phenyl-1'–Nitro-m-Terphenyl.

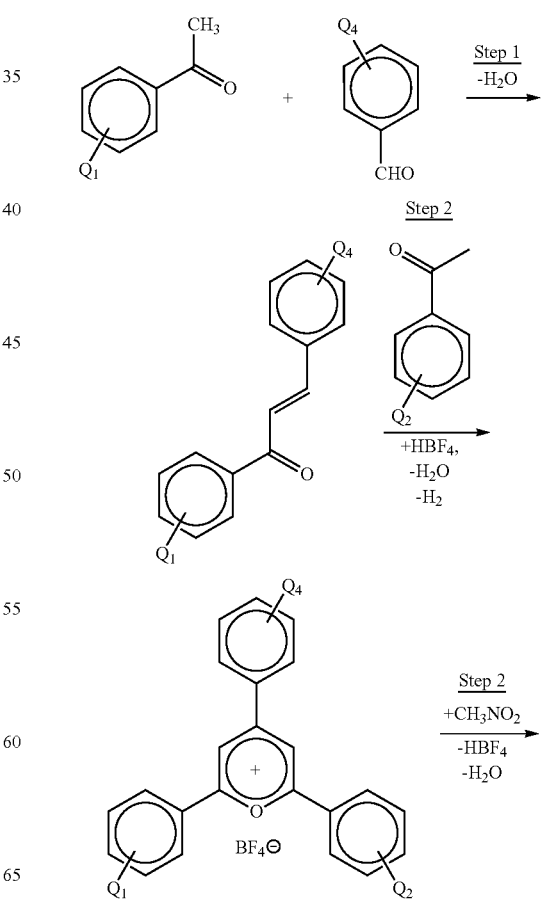

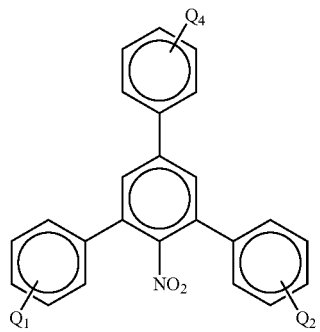

Figure 9:
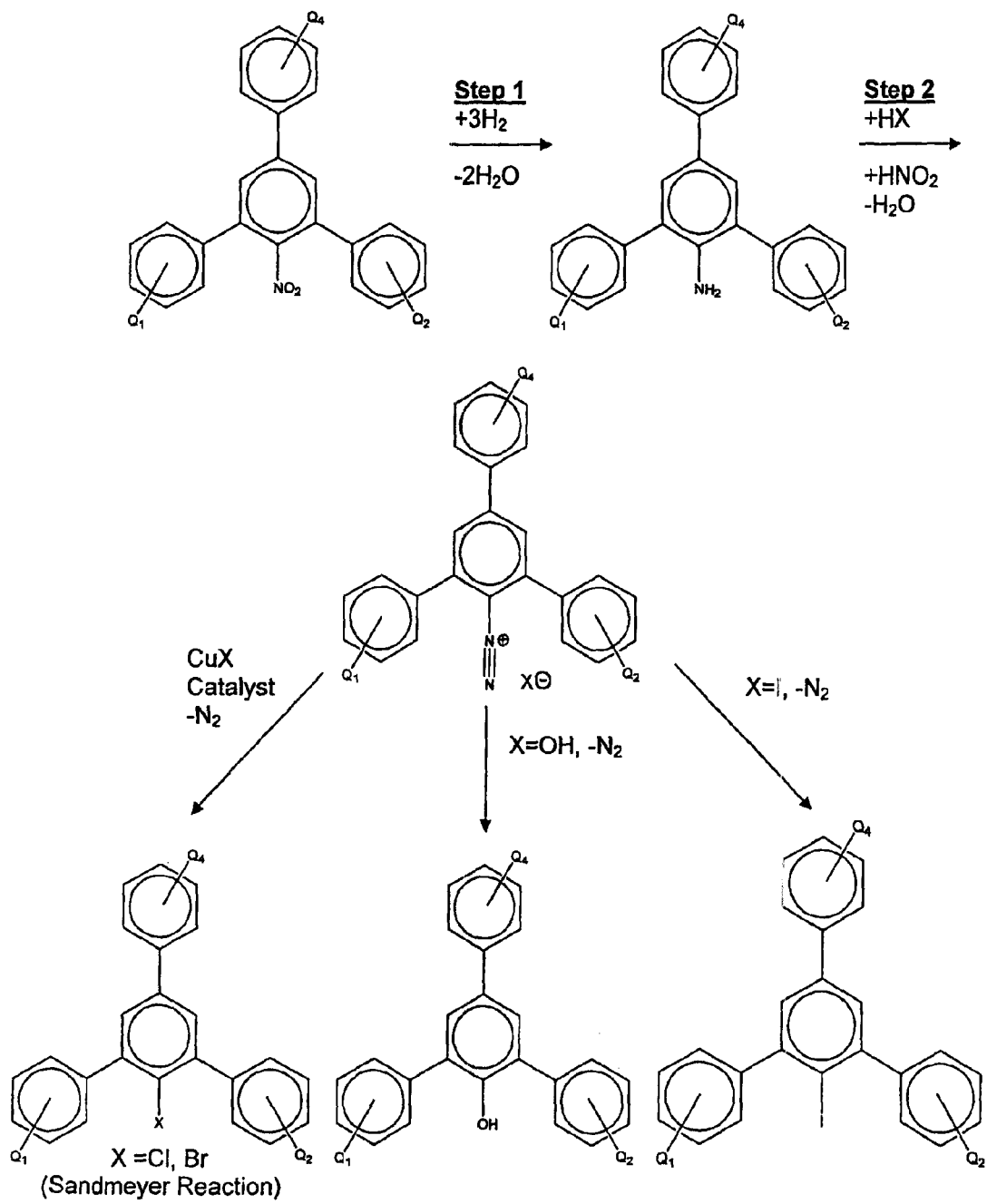
FIG. 9 Conventional Process for the Production of Useful 4'-Phenyl-m-Terphenyl Intermediates with Reactive Amino, Diazo, Halogen and Hydroxy Functionality.
Figure 10:
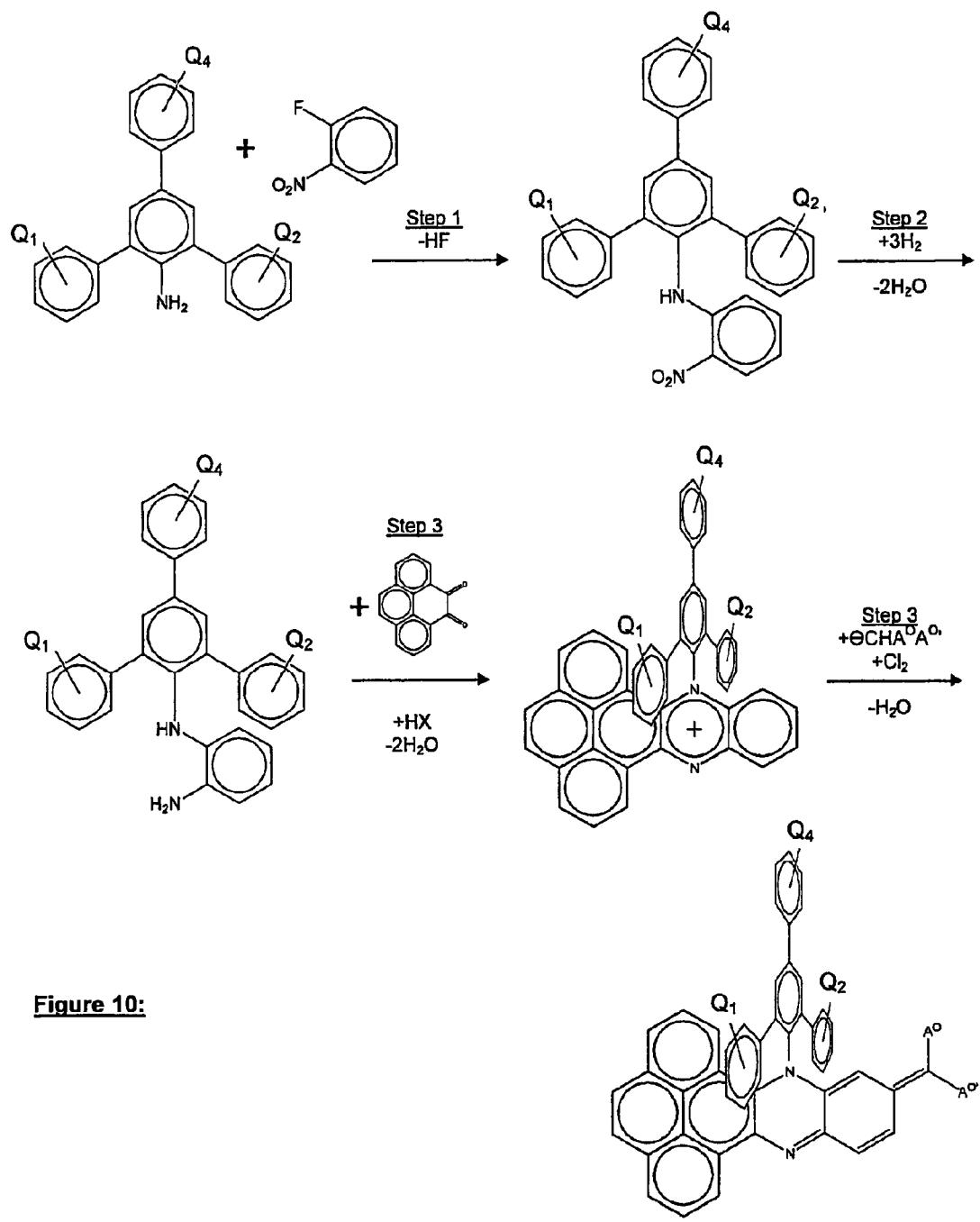
FIG. 10 Specific Nonlimiting Examples of Introduction of Spacer 4'-Phenyl-m-Terphenyl Functionality into a Novel Chromophore System with a 1'-Amino-4'-Phenyl-m-Terphenyl Key Intermediate.
Figure 12:
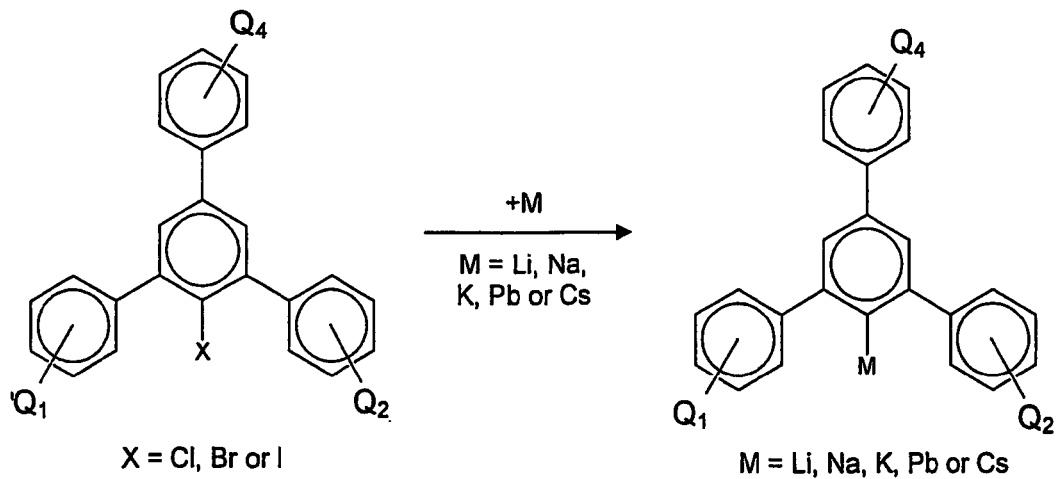
FIG. 12 Conventional Processes for the Production of Useful Organometallic 4'-Phenyl-m-Terphenyls by Reaction with Periodic Group IA Metals with the Halogen Functionality of 1'-Halo-4'-Phenyl-m-Terphenyls.
Figure 13:
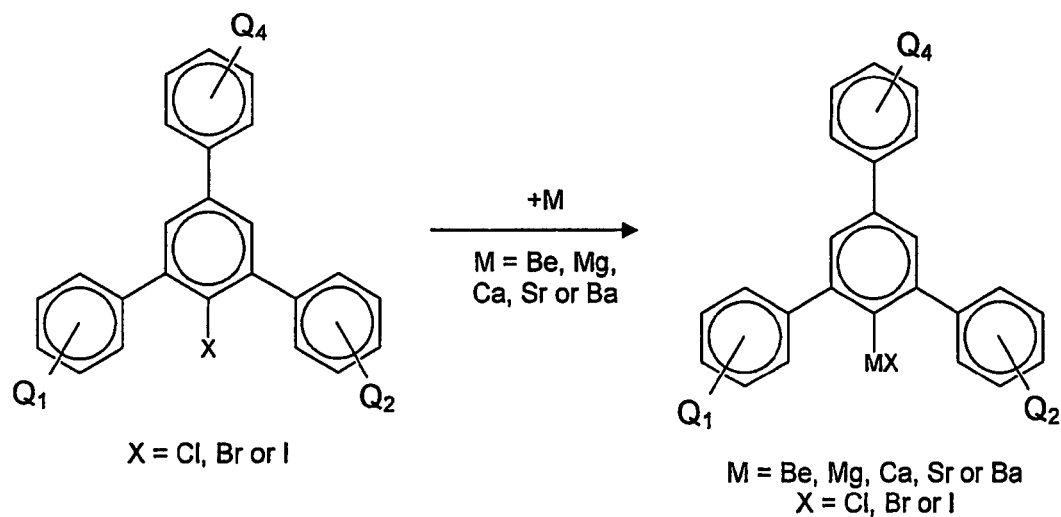
FIG. 13 Conventional Processes for the Production of Useful Organometallic 4'-Phenyl-m-Terphenyl Intermediates by Reaction with Periodic Group IIA Metals with the Halogen Functionality of 1'-Halo-4'-Phenyl-m-Terphenyls.

Key Intermediate for Introduction of 4'-Phenyl-m-Terphenyl Functionality: A 4'-Phenyl-1'-Nitro-m-Terphenyl With reference to scheme 1 above, a compound of Formula I may be prepared by treating a 1-phenyl-ethanone substituted by a Q group ($Q^1$) with a benzaldehyde substituted with $Q^3$ to provide a 1,3-diphenyl-propenone where both phenyl groups are substituted. A second 1-phenyl-ethanone with Q4 substitution is reacted with the 1,3-diphenyl-propenone to produce the 2,4,6 triphenyl substituted pyranyl intermediate. The pyranyl intermediate is converted to a 2'-Nitro-[1,1'; 3',1"]terphenyl with phenyl substitution at the 5 position of the central ring. Additional chemistry may be performed on the nitro functional group to provide any number of labile functional groups that will be reactive with desired binding sites on a nonlinear optical chromophore. FIG. 9 demonstrates how the terphenyl nitro can be easily converted to an amine via hydrogenation. The amine can then serve as a labile group to bond to a chromophore as depicted in FIG. 10 or as a means to make any number of labile functional groups via a diazonium intermediate as depicted in FIG. 9. Specific examples illustrated in FIG. 9 include the manufacture of hydroxyl and halo terphenyls. Halo terphenyls are particularly useful because they may serve as intermediates in the production of synthetically desirable organometallic terphenyl compounds as depicted in FIG. 12 or Grignard reagents as depicted in FIG. 13.

Figure 11:
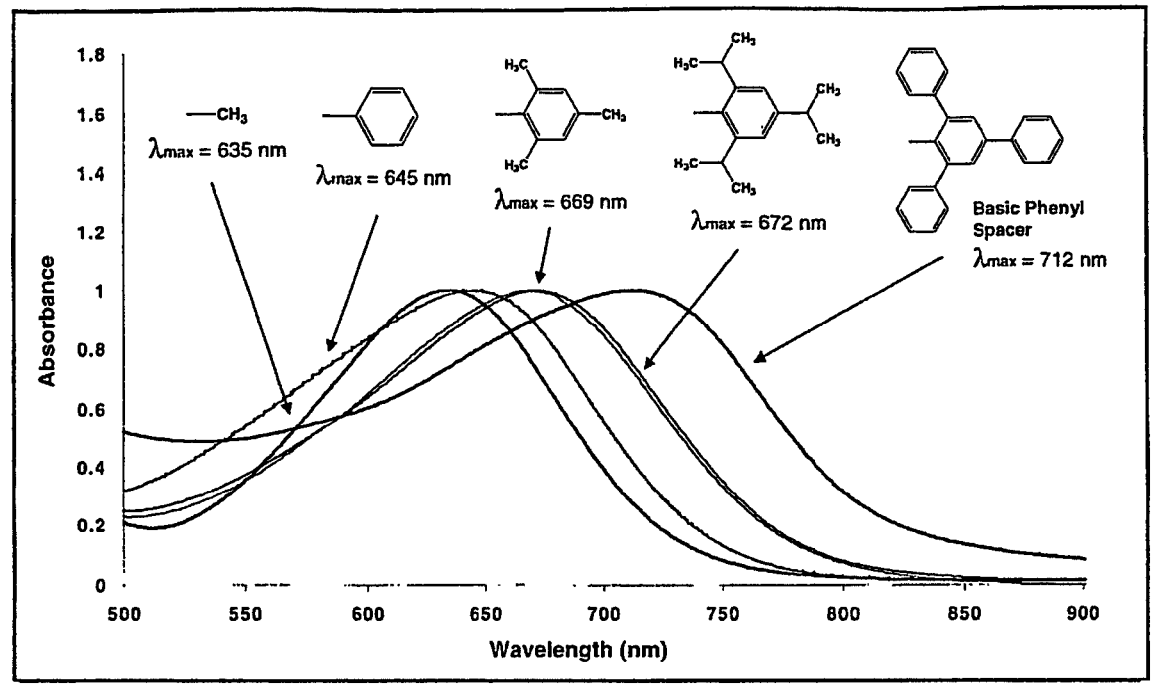
FIG. 11 Visible Absorption Spectra of Chromophores compared to Spacer System with the 4'-phenyl-m-terphenyl Spacer Function.
Figure 11:
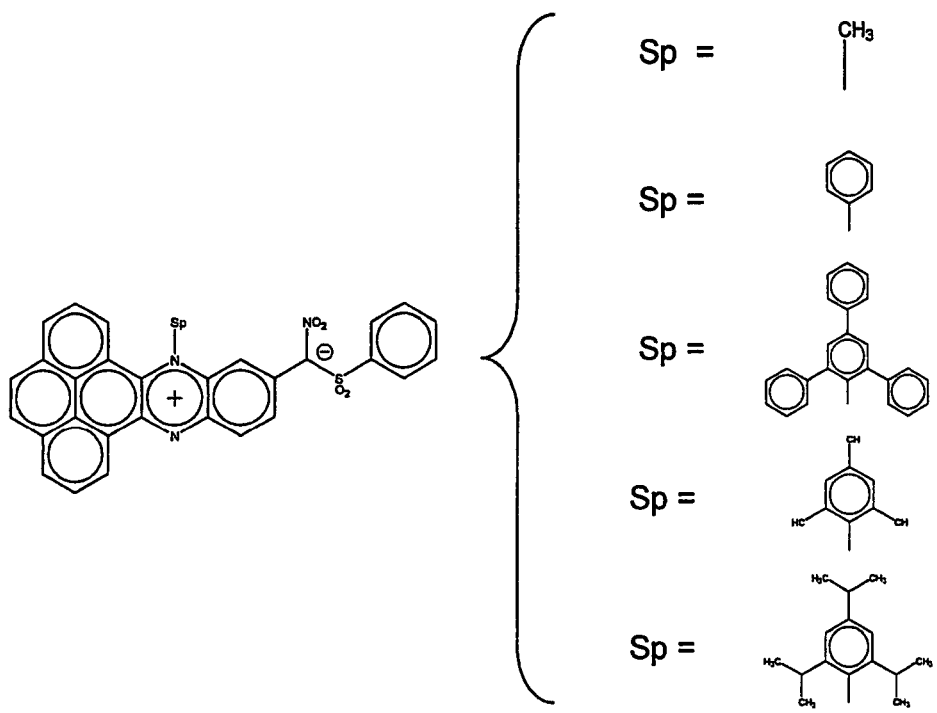

FIG. 11 provides a comparison of the visible absorption spectra of various functional groups attached to the same nonlinear optical chromophore (PTO). The terphenyl spacer with phenyl substitution in the $R^4$ position has the highest λmax at 712 nm. The spacer with the next longest λmax is the 1,3,5-Triisopropyl-benzene group at 672 nm. The advantage of a tricyclic system having a central cyclic structure flanked by two additional cyclic structures only one bond length from the point of attachment to the chromophore is demonstrated by the longer wavelength of the terphenyl spacer. Without being bound to any specific theory it is believed that the increased size of the spacer and the unique geometry of the tricyclic spacer system prevents interaction of the chromophore with solvent molecules thereby inducing an absorption spectrum where the higher λmax indicates a larger exclusion radius which preserves the optical characteristics of the chromophore. When polar aprotic solvent molecules surround the highly polar chromophore core, the solvents align in a low energy configuration to oppose the dipole of the chromophore effectively creating a localized electric field. This electric field alters the ground state CT energy of the chromophore changing its photonic absorption in a fashion known as solvatochromism. The spacer systems exclude the approach of the solvent molecules thus reducing the overall field strength.

An alternative tricyclic spacer system is depicted in Scheme 2 wherein the central $R^3$ cyclic moiety is an indole and $R^1$ and $R^2$ are both phenyl groups having methoxy Q groups. $R^4$ is a chemical bond and $Q^4$ is methoxy.

Scheme 2

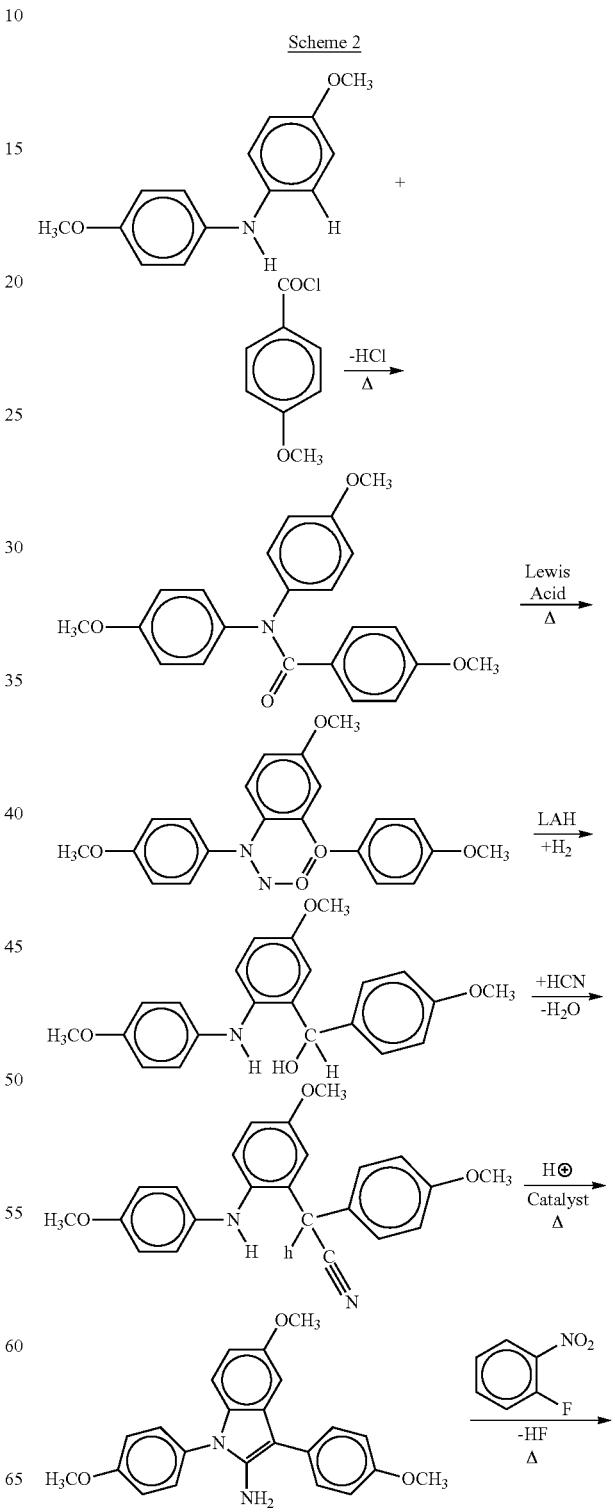

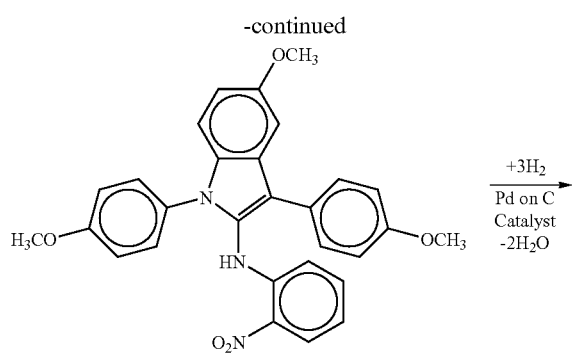
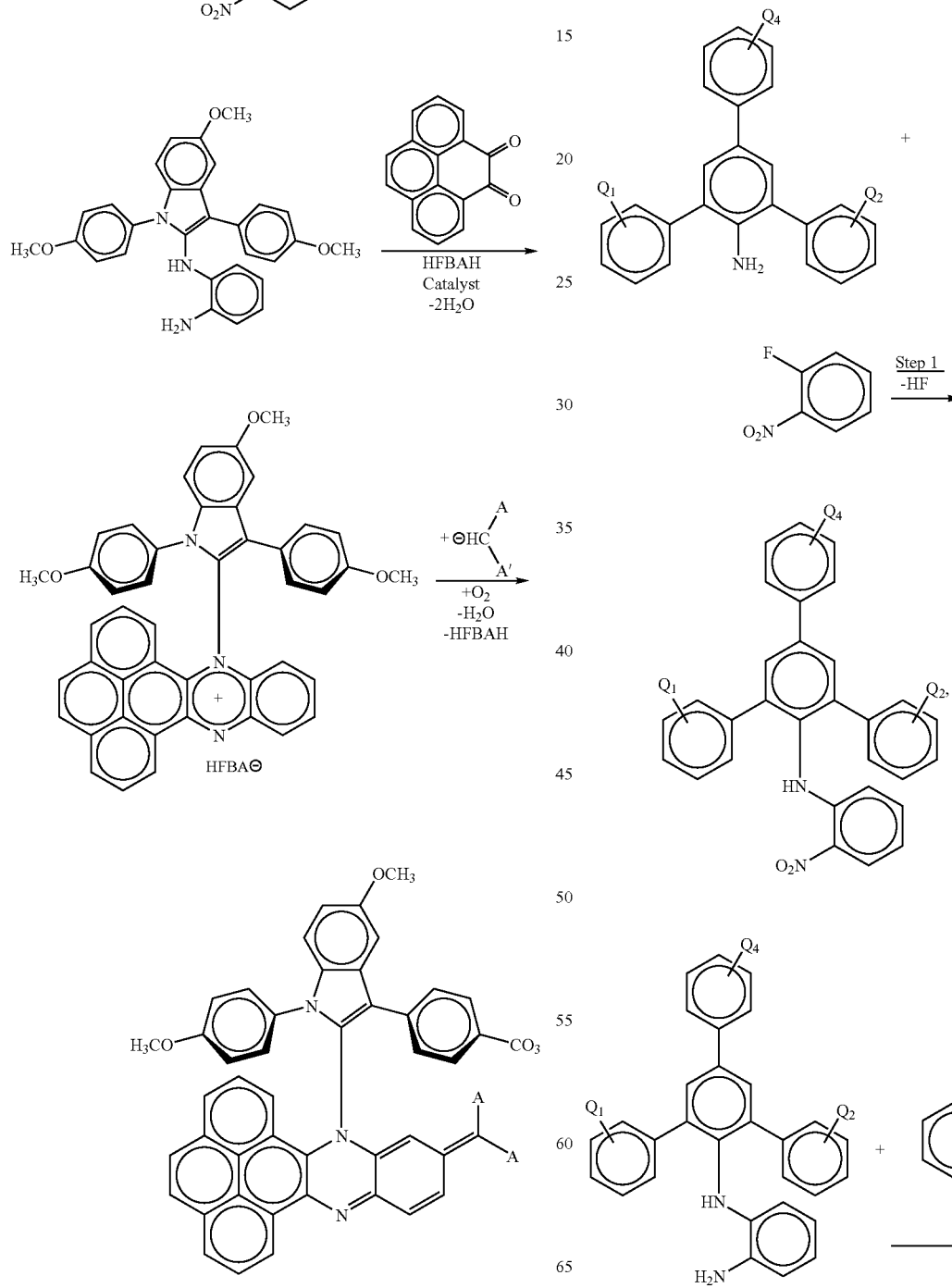
The present invention is illustrated by the following Examples. It will be understood, however, that the invention is not limited by the specific details of the following Examples.
Example 1
Preparation 4'-Phenyl-m-Terphenyl Functionality into a Novel Chromophore (PTØ) (wherein A=NO2) with a 1'-Amino4'-Phenyl-m-Terphenyl Key Intermediate

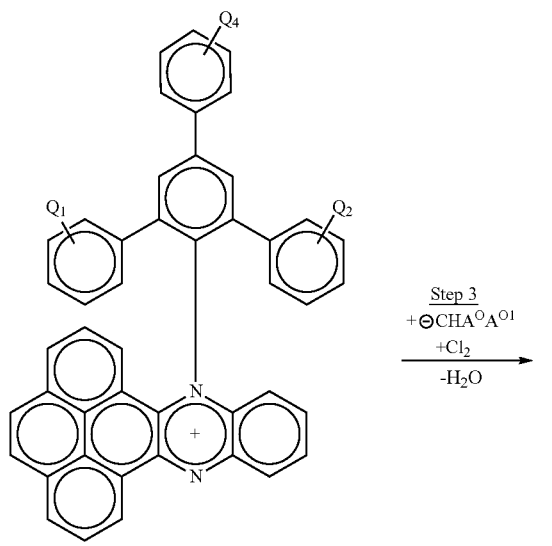
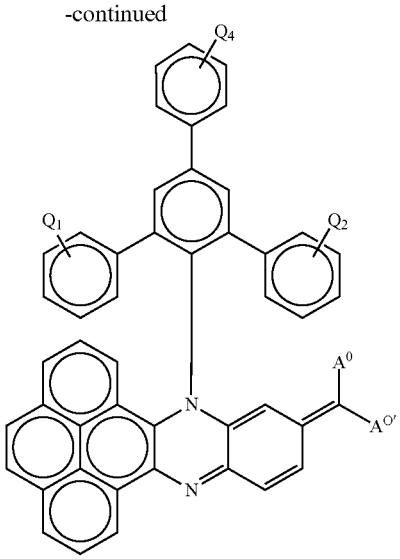
Example 2
Preparation of 1,3-Bis-(4'-methoxy-biphenyl4-yl)-5-(4-methoxy-phenyl)-1H-indole Spacer with Attached Chromophore (PTØ) wherein A=NO$_2$.
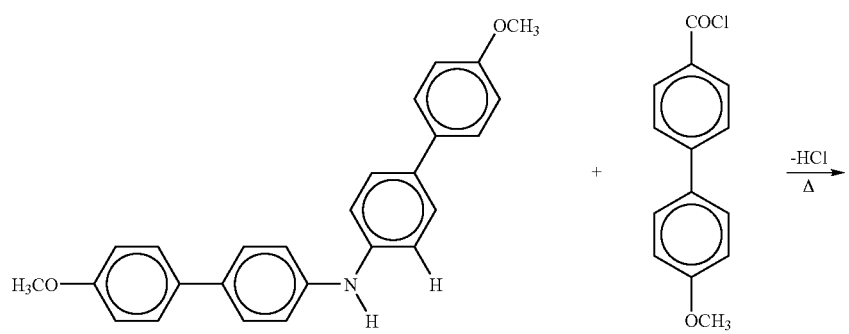
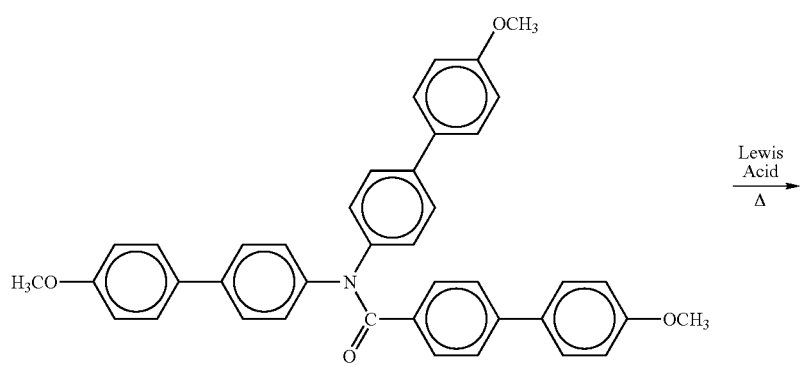

-continued
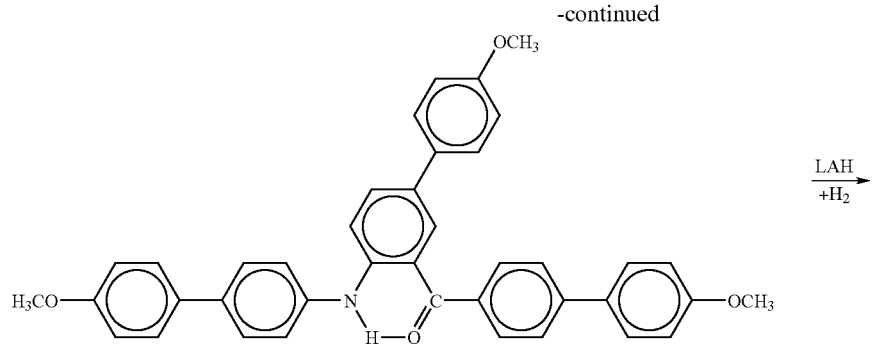
LAH
+H₂ →
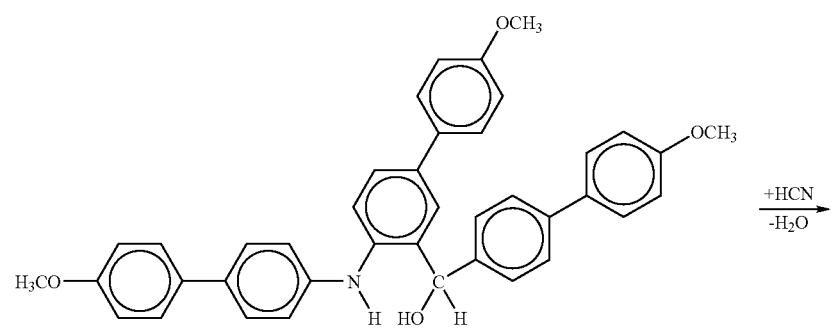
+HCN
-H₂O →
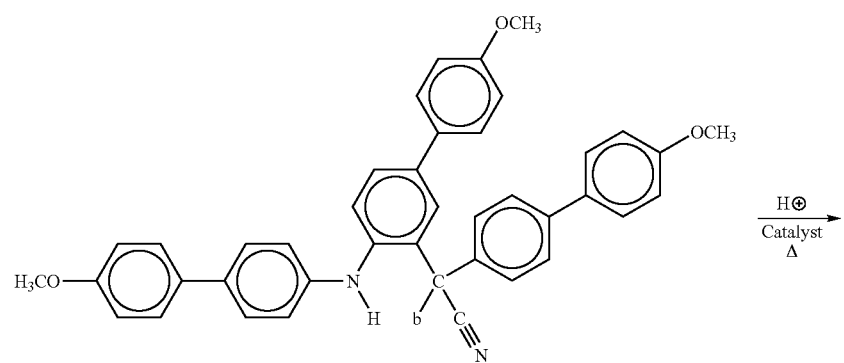
H⊕
Catalyst
Δ →
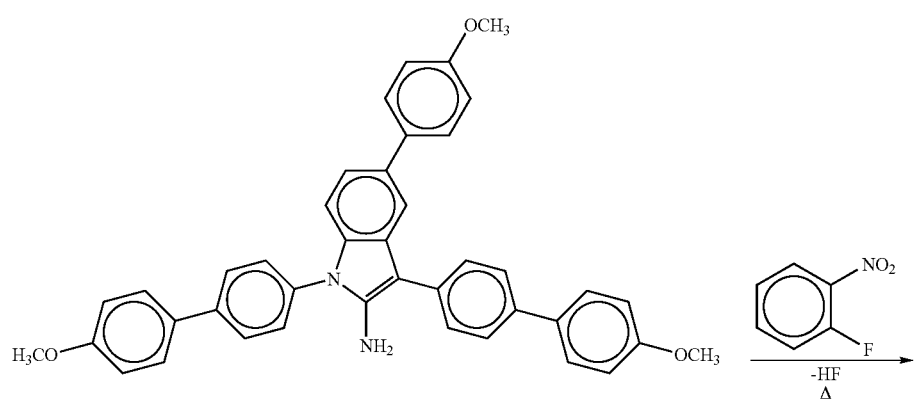
-HF
Δ →

-continued
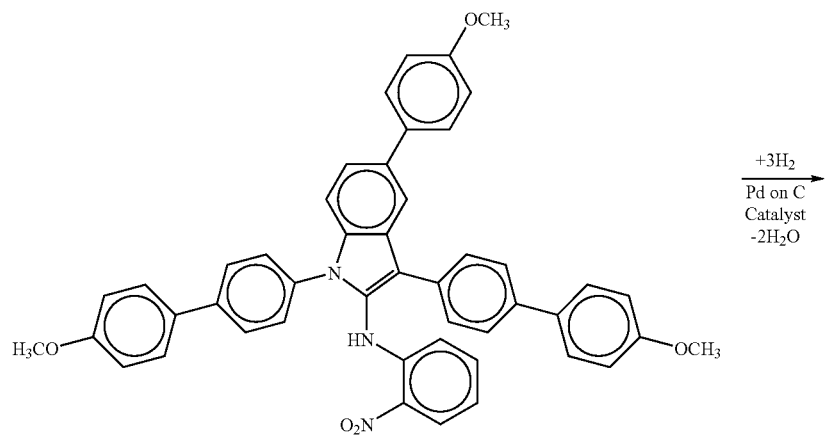
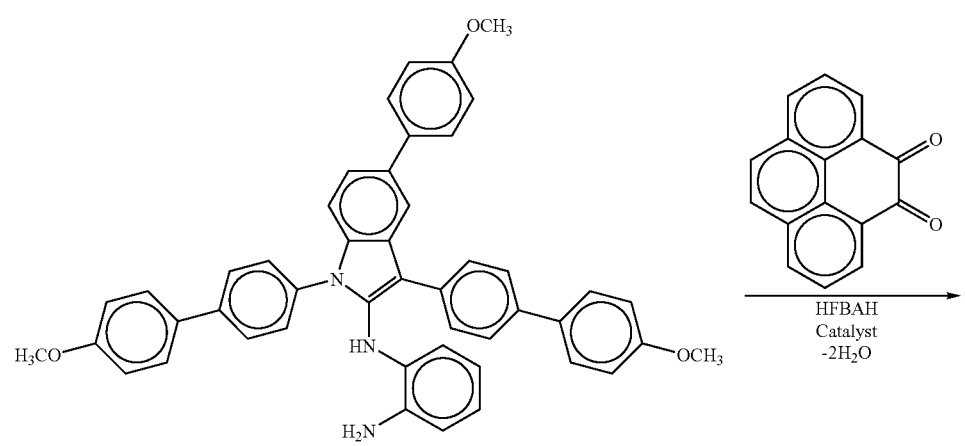
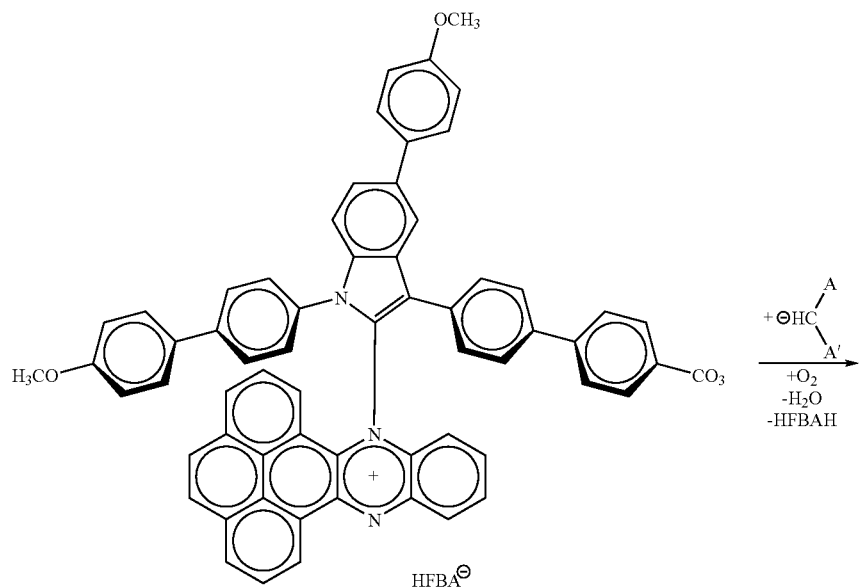

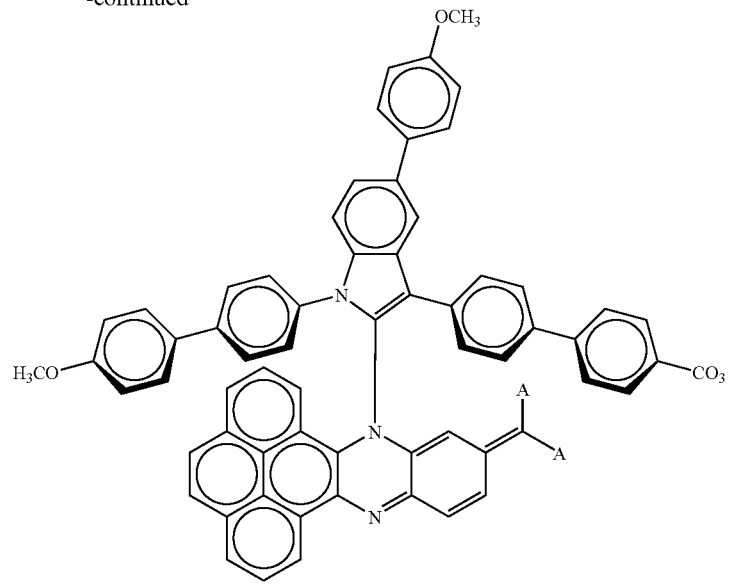
Example 3
Specific Nonlimiting Conventional Synthetic Scheme for the Production of a Spacer System wherein the $R_3$ Ring System is the Heterocyclic Indole Nucleus with a 5-Methoxy Substituent and wherein the $R_1$ and $R_2$ are Respectively the Heterocyclic 2-(1,3,4-Thiadiazole) Nucleus with a 5-Methoxy Substituent and a 4-Anisyl Substituents
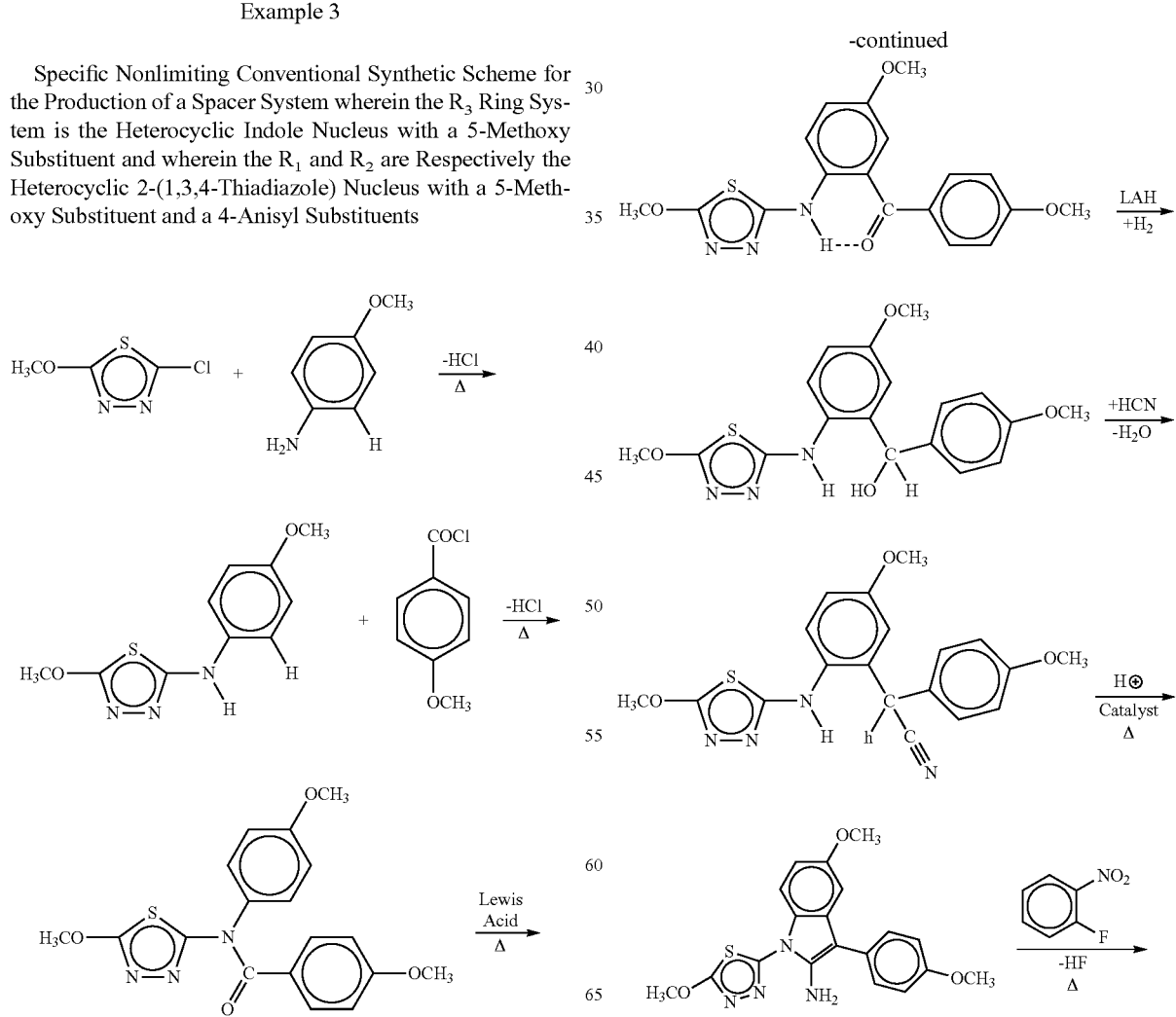

-continued
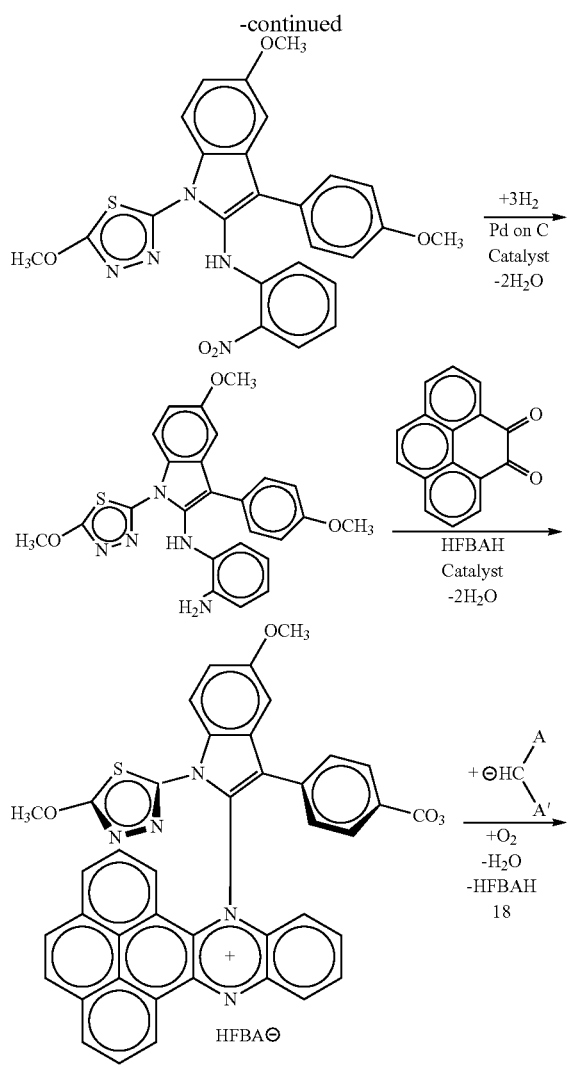
Example 4
Specific Nonlimiting Conventional Synthetic Scheme for the Production of a Spacer System wherein the $R_3$ Ring System is the Heterocyclic Indole Nucleus with a 5-Methoxy Substituent and wherein the $R_1$ and $R_2$ are the Heterocyclic 2-(1,3,4-Thiadiazole) Nuclei
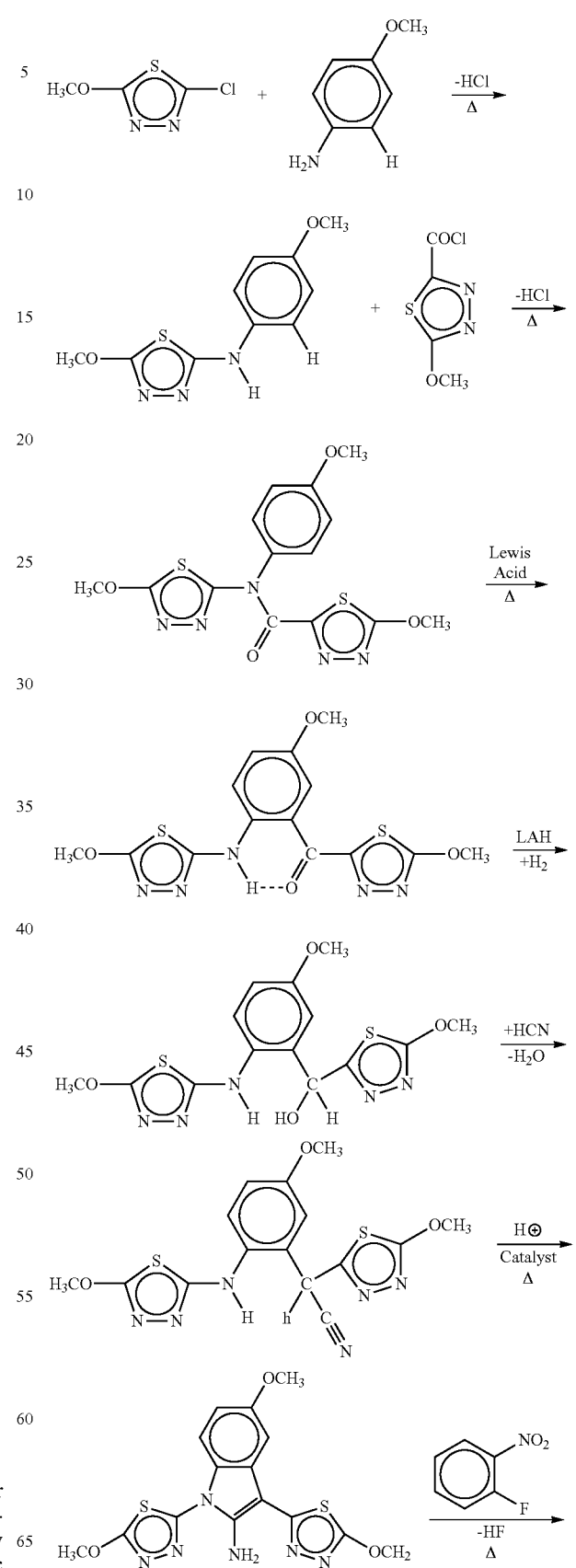

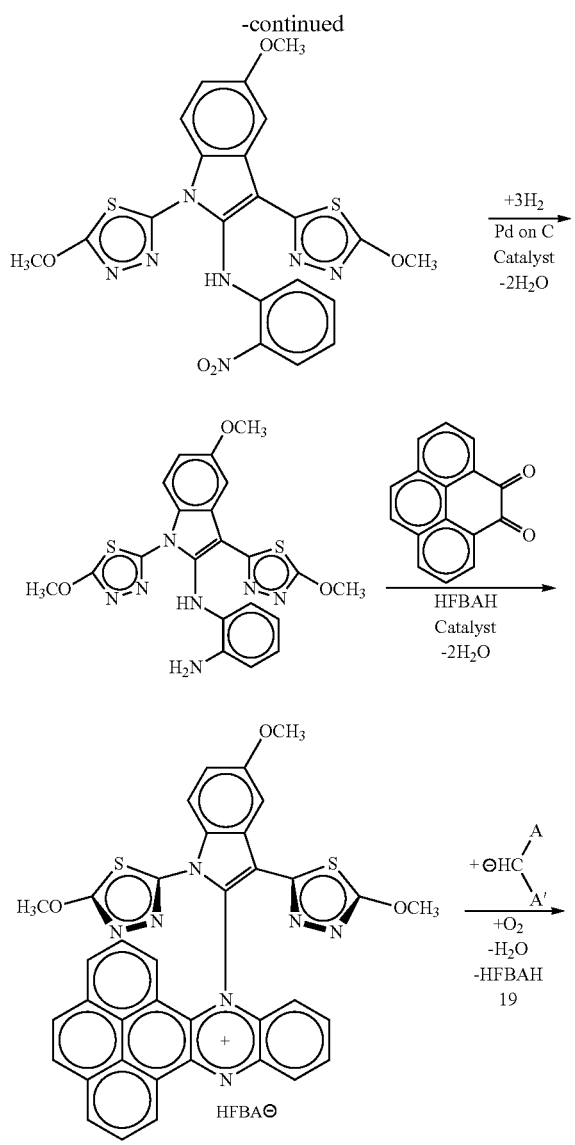

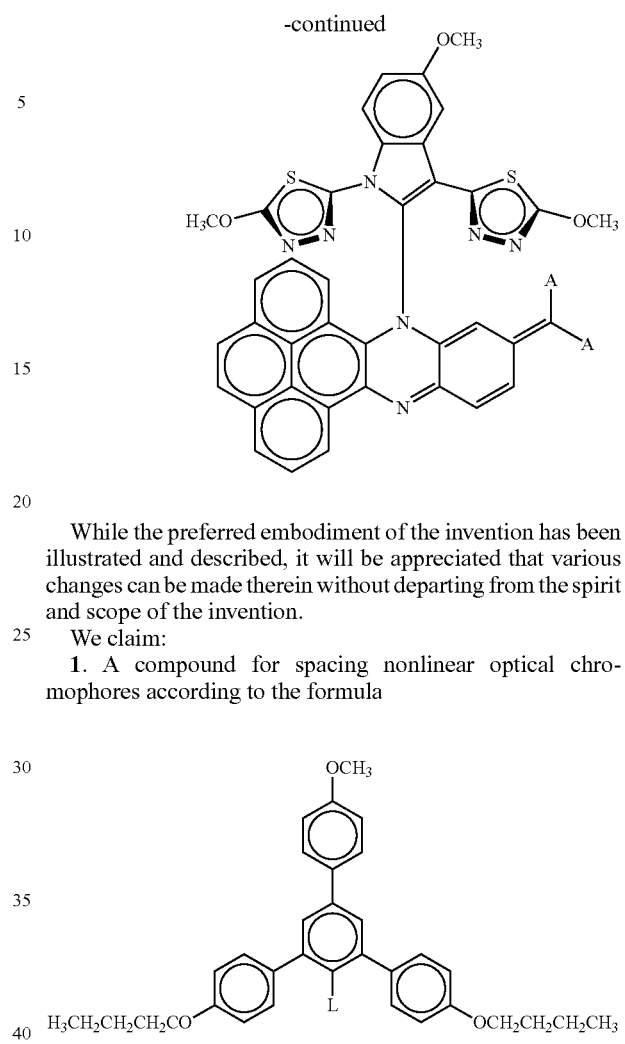

While the preferred embodiment of the invention has been illustrated and described, it will be appreciated that various changes can be made therein without departing from the spirit and scope of the invention.

We claim:

1. A compound for spacing nonlinear optical chromophores according to the formula wherein L represents a labile group selected from the group consisting of hydroxyl groups, alkoxy groups, nitro groups, amines and halogens.

\* \* \* \* \*